US012688572B2

(12) United States Patent
Kawczynski et al.

(10) Patent No.: US 12,688,572 B2
(45) Date of Patent: Jul. 21, 2026

(54) USING DEEP LEARNING TO PROCESS IMAGES OF THE EYE TO PREDICT VISUAL ACUITY

(71) Applicant: Genentech, Inc., South San Francisco, CA (US)

(72) Inventors: Michael G. Kawczynski, South San Francisco, CA (US); Thomas Bengtsson, South San Francisco, CA (US); Jian Dai, South San Francisco, CA (US); Simon S. Gao, South San Francisco, CA (US); Jeffrey R. Willis, South San Francisco, CA (US)

(73) Assignee: Genentech, Inc., South San Francisco, CA (US)

( * ) Notice: Subject to any disclaimer, the term of this patent is extended or adjusted under 35 U.S.C. 154(b) by 332 days.

(21) Appl. No.: 17/590,816

(22) Filed: Feb. 1, 2022

(65) Prior Publication Data

US 2022/0230300 A1     Jul. 21, 2022

Related U.S. Application Data

(63) Continuation of application No. PCT/US2020/044652, filed on Jul. 31, 2020.

(Continued)

(51) Int. Cl.
*G06T 7/00* (2017.01)
*A61B 3/10* (2006.01)
(Continued)

(52) U.S. Cl.
CPC ............ *G06T 7/0004* (2013.01); *A61B 3/102* (2013.01); *G16H 10/20* (2018.01); *G16H 30/40* (2018.01);
(Continued)

(58) Field of Classification Search
CPC ......... G06T 7/0004; G06T 2207/10081; G06T 2207/20081; G06T 2207/20084;
(Continued)

(56) References Cited

U.S. PATENT DOCUMENTS

| 2017/0119243 A1* | 5/2017 | Irvine | .................. A61B 3/102 |
| 2018/0161098 A1* | 6/2018 | Gupta | .................. G06N 20/20 |

(Continued)

FOREIGN PATENT DOCUMENTS

| WO | 2019193362 A2 | 10/2019 | |
| WO | WO-2020200087 A1 * | 10/2020 | ............... A61B 3/00 |

OTHER PUBLICATIONS

Learning to Analyze the Prognostic Value of Current Imaging Biomarkers in Neovascular Age-Related Macular Degeneration, OphthalmologyRetina, Jan. 1, 2018 (Year: 2018).*

(Continued)

*Primary Examiner* — Jennifer Mehmood
*Assistant Examiner* — Heath E. Wells
(74) *Attorney, Agent, or Firm* — Haynes and Boone, LLP

(57) ABSTRACT

Systems and methods disclosed herein relate to using a machine-learning model to process an input of a subject's eye and to predict a current or future visual acuity of the subject. The subject may have been diagnosed with age-related macular degeneration. The predicted current or future visual acuity may be used to (for example) facilitate diagnosing the subject (e.g., with a particular type of age-related macular degeneration), facilitate identifying a treatment strategy for the subject, and/or facilitate designing a clinical study.

21 Claims, 19 Drawing Sheets

Related U.S. Application Data

(60) Provisional application No. 62/990,354, filed on Mar. 16, 2020, provisional application No. 62/940,989, filed on Nov. 27, 2019, provisional application No. 62/907,014, filed on Sep. 27, 2019, provisional application No. 62/882,354, filed on Aug. 2, 2019.

(51) Int. Cl.
  *G16H 10/20*          (2018.01)
  *G16H 30/40*          (2018.01)

(52) U.S. Cl.
  CPC ............... *G06T 2207/10081* (2013.01); *G06T 2207/20081* (2013.01); *G06T 2207/20084* (2013.01); *G06T 2207/30041* (2013.01)

(58) Field of Classification Search
  CPC ......... G06T 2207/30041; G06T 7/0012; G06T 5/70; G06T 11/003; G06T 2207/10101; A61B 3/102; A61B 3/103; A61B 3/12; A61B 3/14; G16H 10/20; G16H 30/40; G16H 50/20; G06N 3/045; G06N 3/08; G06N 20/00
  USPC ........................................................ 382/185
  See application file for complete search history.

(56)                References Cited

U.S. PATENT DOCUMENTS

| | | | | |
|---|---|---|---|---|
| 2019/0110753 | A1* | 4/2019 | Zhang | A61B 3/0025 |
| 2019/0180441 | A1* | 6/2019 | Peng | G06T 7/0016 |
| 2020/0288971 | A1* | 9/2020 | Huang | G06T 7/168 |
| 2021/0228073 | A1* | 7/2021 | Park | G16H 50/20 |
| 2021/0357696 | A1* | 11/2021 | Peng | G16H 50/30 |
| 2022/0181007 | A1* | 6/2022 | Meyers-Normand | |
| | | | | G16H 30/00 |
| 2022/0207729 | A1* | 6/2022 | Boyd | G06V 10/774 |
| 2023/0419485 | A1* | 12/2023 | Niemeijer | G06F 18/2148 |

OTHER PUBLICATIONS

DeepSeeNet: A deep learning model for automated classification of patient-based age-related macular degeneration severity from color fundus photographs, Peng, Yifan, Dharssi, Shazia Chen, Qingyu Keenan, Tiarnan D. Agron, Elvira, Wong, Wai T. ,Chew, Emily Y. • Lu, Zhiyong Ophthalmology. (Year: 2018).*

Deep Convolutional Neural Network Based Screening And Assessment Of Age-Related Macular Degeneration From Fundus Images, by Arun Govindaiah, Md. Akter Hussain, Roland Theodore Smith, and Alauddin Bhuiyan, 2018 IEEE 15th International Symposium on Biomedical Imaging (ISBI 2018) Apr. 4-7, 2018 (Year: 2018).*

International Search Report and Written Opinion mailed Dec. 11, 2020 in related application PCT/US2020/044652, 21 pages.

Burlina et al., "Automated Grading of Age-Related Macular Degeneration From Color Fundus Images Using Deep Convolutional Neural Networks," JAMA Ophthalmology, Sep. 28, 2017, 7 pages.

International Preliminary Report on Patentability issued Feb. 8, 2022 in related application PCT/US2020/044652, 13 pages.

American Foundation for the Blind, "Statistical Snapshots from the American Foundation for the Blind," [Retrieved from the Internet]. [Retrieved on Nov. 11, 2024 from https://www.afb.org/research-and-initiatives/statistics], 4 pages.

Aslam et al., "Use of a Neural Net to Model the Impact of Optical Coherence Tomography Abnormalities on Vision in Age-Related Macular Degeneration," American Journal of Ophthalmology, vol. 185, Jan. 2018, pp. 94-100, 22 pages.

Brown et al., "Ranibizumab versus Verteporfin for Neovascular Age-Related Macular Degeneration," The New England Journal of Medicine, 355(14), pp. 1432-1444, Oct. 5, 2006, 13 pages.

Busbee et al., "Twelve-Month Efficacy and Safety of 0.5 mg or 2.0 mg Ranibizumab in Patients with Subfoveal Neovascular Age-related Macular Degeneration", American Academy of Ophthalmology, Elsevier, vol. 120, Issue 5, pp. 1046-1056, May 2013, 11 pages.

Filho et al., "Outer Retinal Layers as Predictors of Vision Loss," Review of Ophthalmology, Apr. 15, 2015. [Retrieved from the Internet], [Retrieved from https://www.reviewofophthalmology.com/article/outer-retinal-layers-as-predictors-of-vision-loss on Nov. 11, 2024], 8 pages.

Issa et al., "Structure-function correlation of the human central retina, "PLoS One, Sep. 2010, vol. 5, Issue 9, pp. e12864, 9 pages.

Maguire et al., "Five-Year Outcomes with Anti-Vascular Endothelial Growth Factor Treatment of Neovascular Age-Related Macular Degeneration: The Comparison of Age-Related Macular Degeneration Treatments Trials." Ophthalmology, vol. 123, Issue 8, Aug. 2016, pp. 1751-1761.

He et al., "Deep Residual Learning for Image Recognition," Proceedings of the IEEE conference on computer vision and pattern recognition, Dec. 2015 (pp. 770-778).

He et al., "Identity Mappings in Deep Residual Networks." Springer Publishing, B. Leibe et al. (Eds.): ECCV 2016, Part IV, LNCS 9908, pp. 630-645, 2016.

Ho et al., "Twenty-four-Month Efficacy and Safety of 0.5 mg or 2.0 mg Ranibizumab in Patients with Subfoveal Neovascular Age-Related Macular Degeneration," American Academy of Ophthalmology, vol. 121, No. 11, Nov. 2014, 12 pages.

Jaffe et al., "Macular Morphology and Visual Acuity in the Comparison of Age-related Macular Degeneration Treatments Trials," Ophthalmology, vol. 120, No. 9, Sep. 2013, pp. 1860-1870.

Karri et al., "Transfer learning based classification of optical coherence tomography images with diabetic macular edema and dry age-related macular degeneration," Biomedical Optics Express 579, vol. 8, No. 2, Feb. 1, 2017.

Krizhevsky et al., "ImageNet Classification with Deep Convolutional Neural Networks," Advances in neural information processing systems, NIPS 2012, pp. 1097-1105.

Lee et al., "Deep Learning Is Effective for Classifying Normal versus Age-Related Macular Degeneration OCT Images," American Academy of Ophthalmology, vol. 1, No. 4, Jul./Aug. 2017, pp. 322-327.

Liu et al., "On the variance of the adaptive learning rate and beyond," ICLR 2020, 14 pages. [Retrieved from the Internet]. [Retrieved from https://arxiv.org/abs/1908.03265].

Mathew et al., "Predictive Value of Spectral-Domain Optical Coherence Tomography Features in Assessment of Visual Prognosis in Eyes With Neovascular Age-Related Macular Degeneration Treated With Ranibizumab," American Journal of Ophthalmology, vol. 155, Issue 4, pp. 720-726, Apr. 2013.

Muether et al., "Delay between medical indication to anti-VEGF treatment in age-related macular degeneration can result in a loss of visual acuity." Graefes Arch. Clin. Exp. Ophthalmol. 249, 633-637 (2011).

Ng, "Feature selection, L 1 vs. L 2 regularization, and rotational invariance." Proceedings of the twenty-first international conference on Machine learning (ACA1). Canada, 2004.

Rohm et al., "Predicting Visual Acuity by Using Machine Learning in Patients Treated for Neovascular Age-Related Macular Degeneration," Ophthalmology, vol. 125, Issue 7, Jul. 2018, pp. 1028-1036.

Rubin et al., "A comprehensive assessment of visual impairment in a population of older Americans. The SEE Study. Salisbury Eye Evaluation Project," Investigative Ophthalmology & Visual Science, Mar. 1997, vol. 38, No. 3, 12 pages.

Russakovsky et al., "ImageNet Large Scale Visual Recognition Challenge." Int J Comput Vis. 2015; 115: 211-252.

Schmidt-Erfurth et al., "Machine Learning to Analyze the Prognostic Value of Current Imaging Biomarkers in Neovascular Age-Related Macular Degeneration," Ophthalmology Retina, vol. 2, No. 1, Jan. 2018.

Schmidt-Erfurth et al.,, "A view of the current and future role of optical coherence tomography in the management of age-related macular degeneration," Eye (2017), 31, pp. 26-44, published online Nov. 25, 2016.

(56) References Cited

OTHER PUBLICATIONS

Schmidt-Erfurth et al., "Pigment epithelial detachment followed by retinal cystoid degeneration leads to vision loss in the treatment of neovascular age-related macular degeneration." Ophthalmology vol. 122, No. 4, Apr. 2015.

Selvaraju et al., "Grad-CAM: Visual Explanations from Deep Networks via Gradient-based Localization," 2019. [Retrieved from the Internet]. [Retrieved from https://arxiv.org/abs/1610.02391 on Nov. 11, 2024].

Sharma et al., "Macular Morphology and Visual Acuity in the Second Year of the Comparison of Age-Related Macular Degeneration Treatments Trials." Ophthalmology. Apr. 2016; 123(4):865-75.

Simonyan et al., Deep Inside Convolutional Networks: Visualising Image Classification Models and Saliency Maps. Apr. 2014. [Retrieved from the Internet]. [Retrieved from https://arxiv.mg/abs/1312.6034 on Nov. 11, 2024].

Springenberg et al., "Striving for simplicity: The all convolutional net." Apr. 2015. [Retrieved from the Internet]. [Retrieved from https://arxiv.org/abs/1412.6806 on Nov. 11, 2024].

Srivastava et al., "Dropout: A Simple Way to Prevent Neural Networks from Overfitting." Journal of Machine Learning Research 15 (2014), pp. 1929-1958.

Ting et al., "Artificial intelligence and deep learning in ophthalmology," British Journal of Ophthalmology, Feb. 2019, vol. 103, Issue 2, pp. 167-175.

Waldstein et al., "Morphology and visual acuity in aflibercept and ranibizumab therapy for neovascular age-related macular degeneration in the View trials." Ophthalmology, vol. 123, No. 7, Jul. 2016.

Alemi, "Improving Inception and Image Classification in TensorFlow," Google Research, Aug. 31, 2016.

Szegedy et al., "Inception-v4, Inception-ResNet and the Impact of Residual Connections on Learning," Aug. 2016 [Retrieved from the Internet]. [Retrieved from https://arxiv.org/abs/1602.07261 on Nov. 11, 2024].

Rosenfeld et al., Ranibizumab for neovascular age-related macular degeneration. New Engl. J. Med. 355(14), 1419-1431 (2006).

Eisner et al., "Relations between fundus appearance and function. Eyes whose fellow eye has exudative age-related macular degeneration." Invest. Ophth. Vis. Sci. 32(1), 8-20 (1991).

Kingma et al., "A method for stochastic optimization." arXiv preprint arXiv:1412.6980 (2014).

Bland et al., "Correlation in restricted ranges of data," BMJ Brit Med, 342:d556, Mar. 11, 2011.

Patel et al., "Intersession Repeatability of Visual Acuity Scores in Age-Related Macular Degeneration," Investigative Ophthalmology & Visual Science, Oct. 2008, vol. 49, No. 10.

Office Action dated Apr. 25, 2024 from related Japanese application No. 2022-506613, 13 pages.

Szegedy et al., "Going Deeper with Convolutions," Proceedings of the IEEE Conference on Computer Vision and Pattern Recognition (CVPR), 2015, pp. 1-9.

Office Action dated Mar. 29, 2025 from related Chinese Application No. 202080055208.7, original and English translation, 20 pages.

* cited by examiner

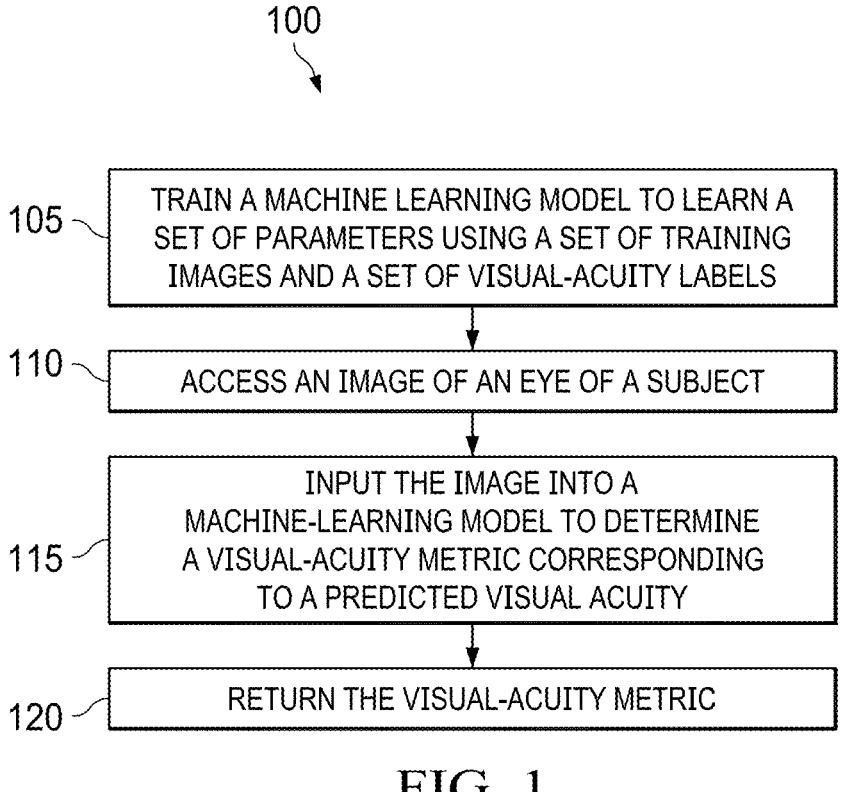

100

105 — TRAIN A MACHINE LEARNING MODEL TO LEARN A SET OF PARAMETERS USING A SET OF TRAINING IMAGES AND A SET OF VISUAL-ACUITY LABELS

110 — ACCESS AN IMAGE OF AN EYE OF A SUBJECT

115 — INPUT THE IMAGE INTO A MACHINE-LEARNING MODEL TO DETERMINE A VISUAL-ACUITY METRIC CORRESPONDING TO A PREDICTED VISUAL ACUITY

120 — RETURN THE VISUAL-ACUITY METRIC

205 — PREDICT A VISUAL ACUITY OF EACH SUBJECT OF A SET OF SUBJECTS

210 — DETERMINE, FOR EACH OF THE SET OF SUBJECTS, WHETHER THE SUBJECT IS ELIGIBLE TO PARTICIPATE IN A CLINICAL STUDY

215 — CONDUCT A CLINICAL STUDY WITH A SUBSET OF SUBJECTS

220 — GENERATE A RESULT OF THE CLINICAL STUDY

FIG. 2

PREDICTED BCVA

ResNet-50 V2

FIG. 5A
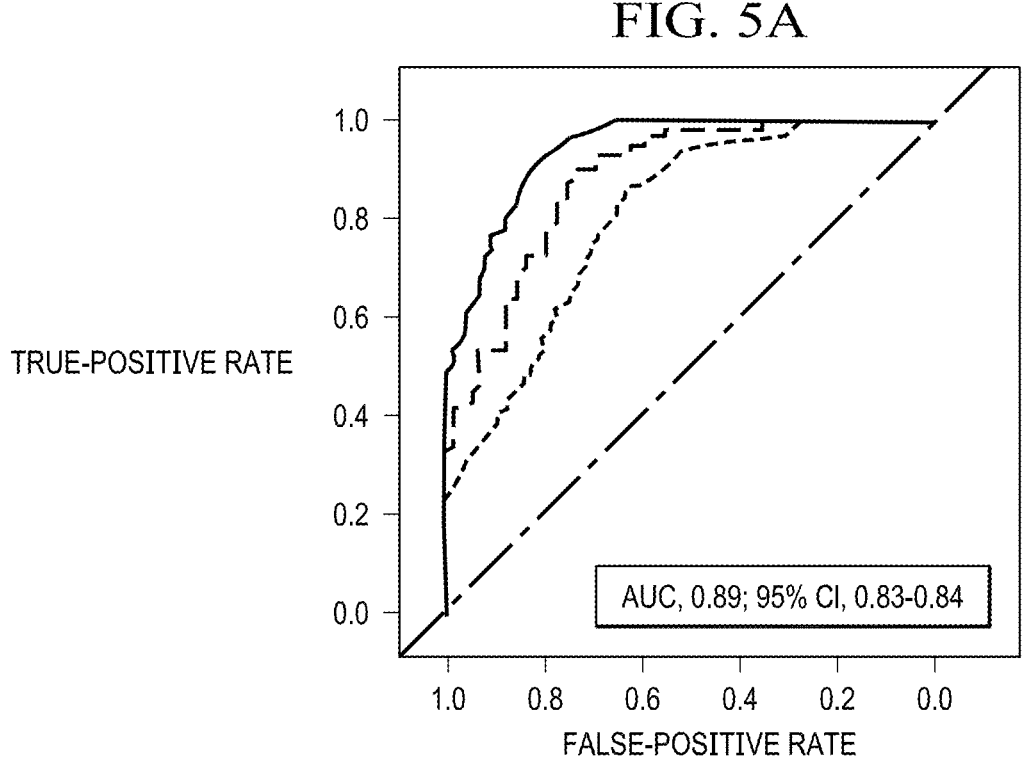
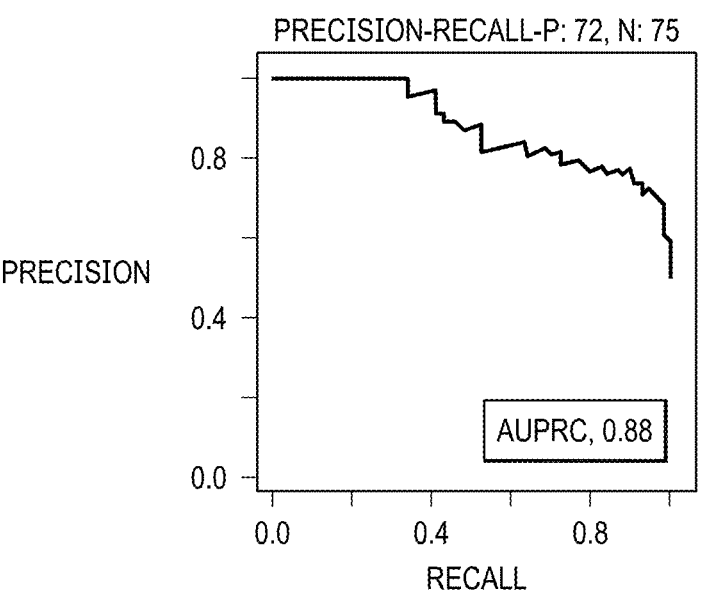

FIG. 5B
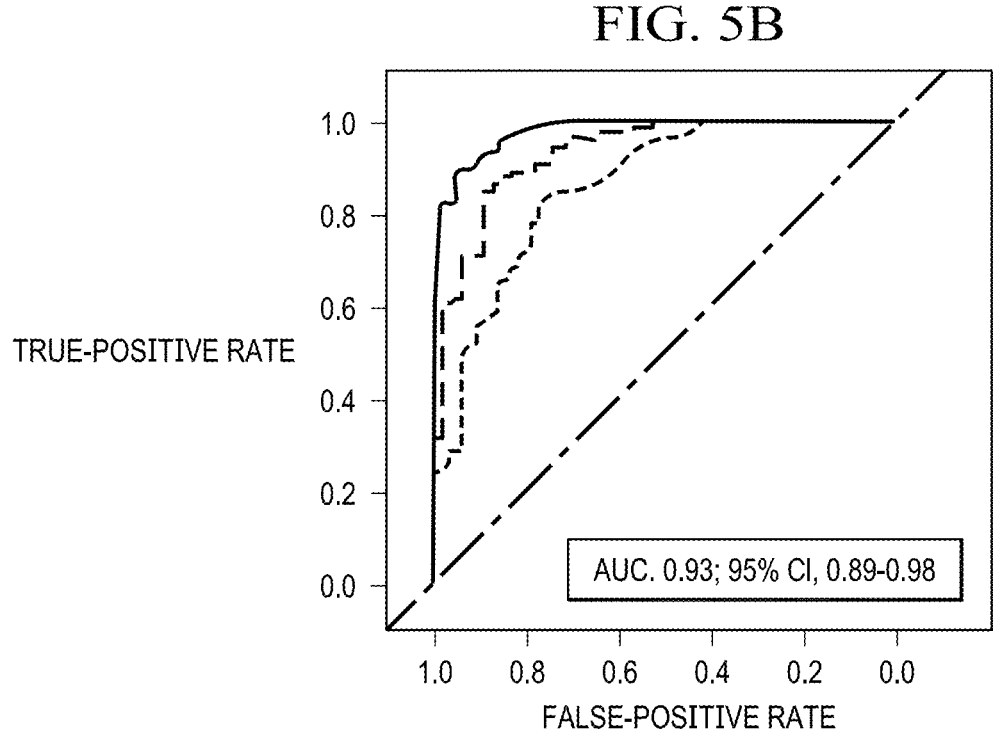
AUC. 0.93; 95% CI, 0.89-0.98
TRUE-POSITIVE RATE
FALSE-POSITIVE RATE
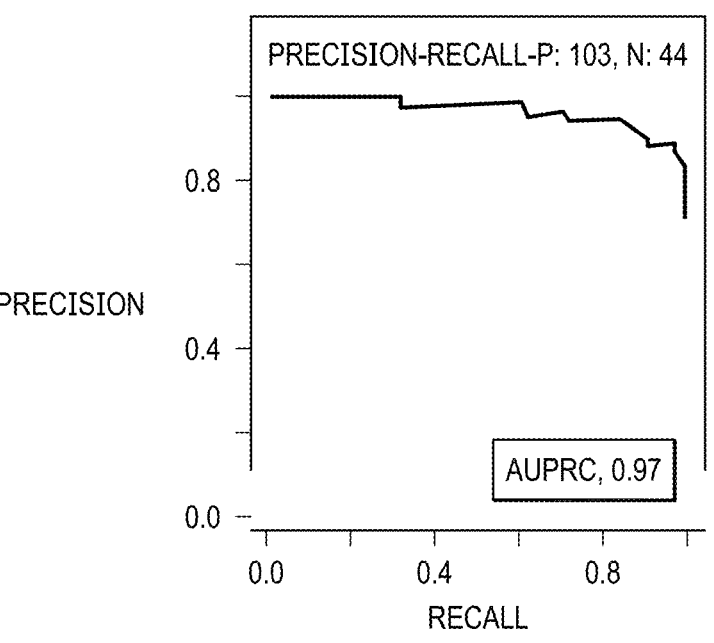
PRECISION-RECALL-P: 103, N: 44
AUPRC, 0.97
PRECISION
RECALL

FIG. 5C
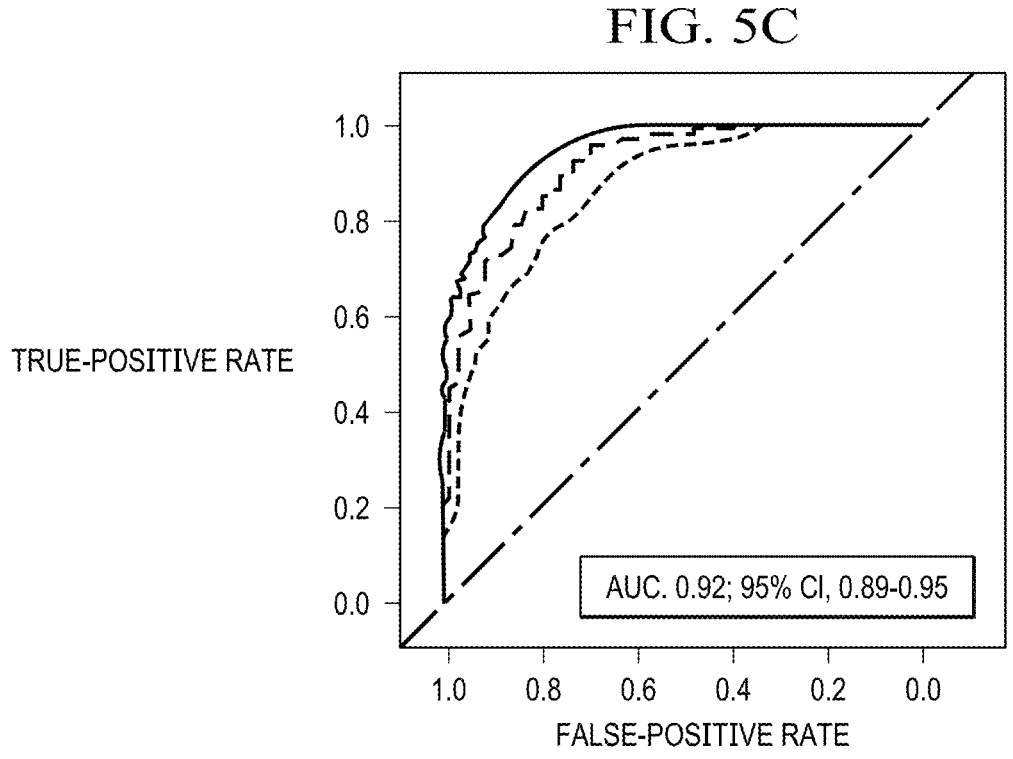
TRUE-POSITIVE RATE
FALSE-POSITIVE RATE
AUC. 0.92; 95% CI, 0.89-0.95
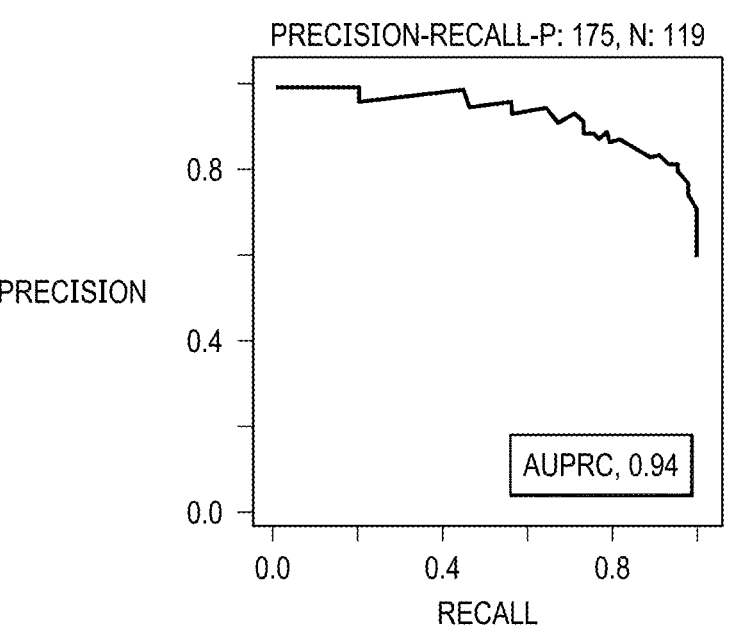
PRECISION-RECALL-P: 175, N: 119
PRECISION
RECALL
AUPRC, 0.94

FIG. 6A

FIG. 7A
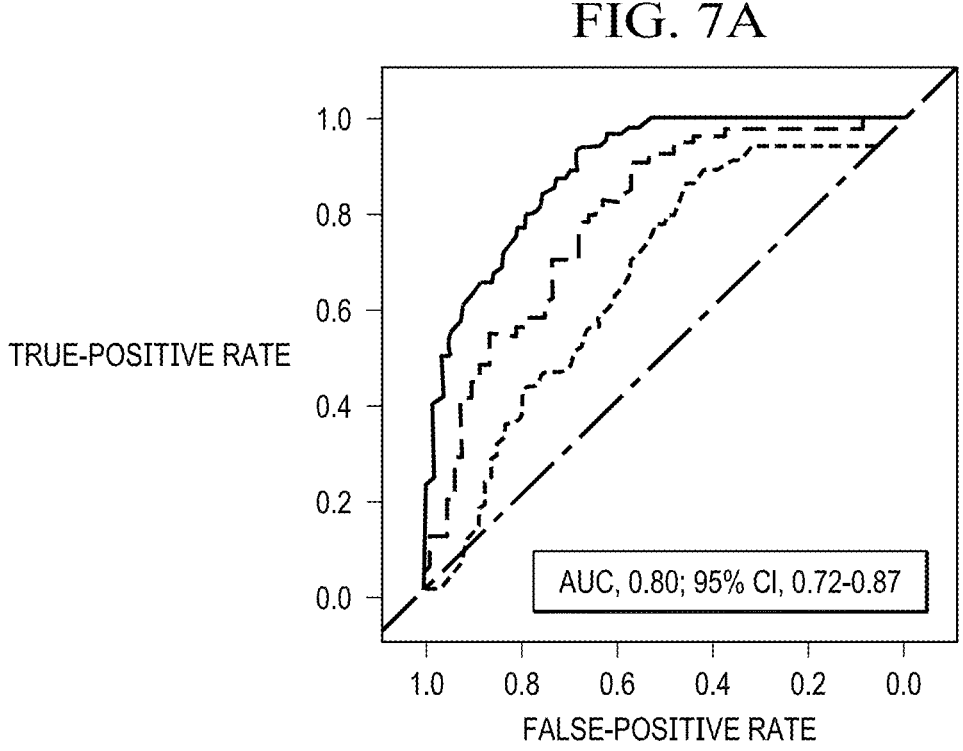
TRUE-POSITIVE RATE
FALSE-POSITIVE RATE
AUC, 0.80; 95% CI, 0.72-0.87
PRECISION-RECALL-P: 58, N: 68
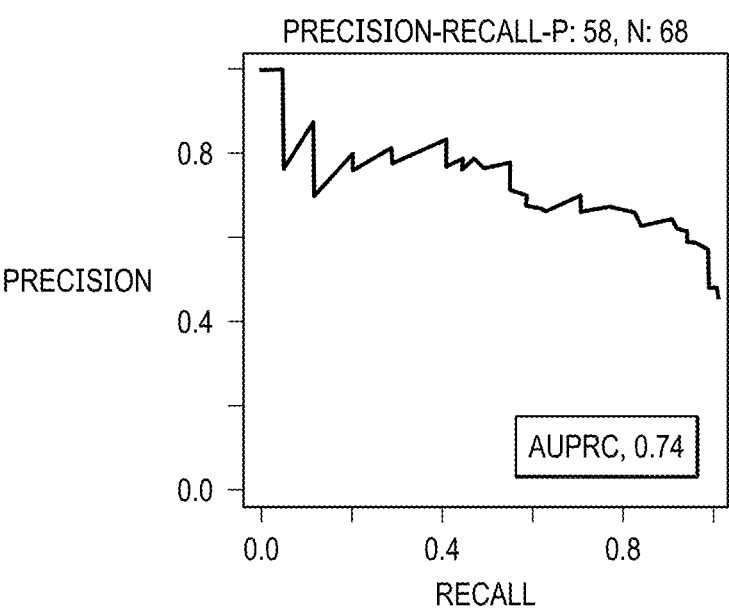
PRECISION
AUPRC, 0.74
RECALL

FIG. 7C
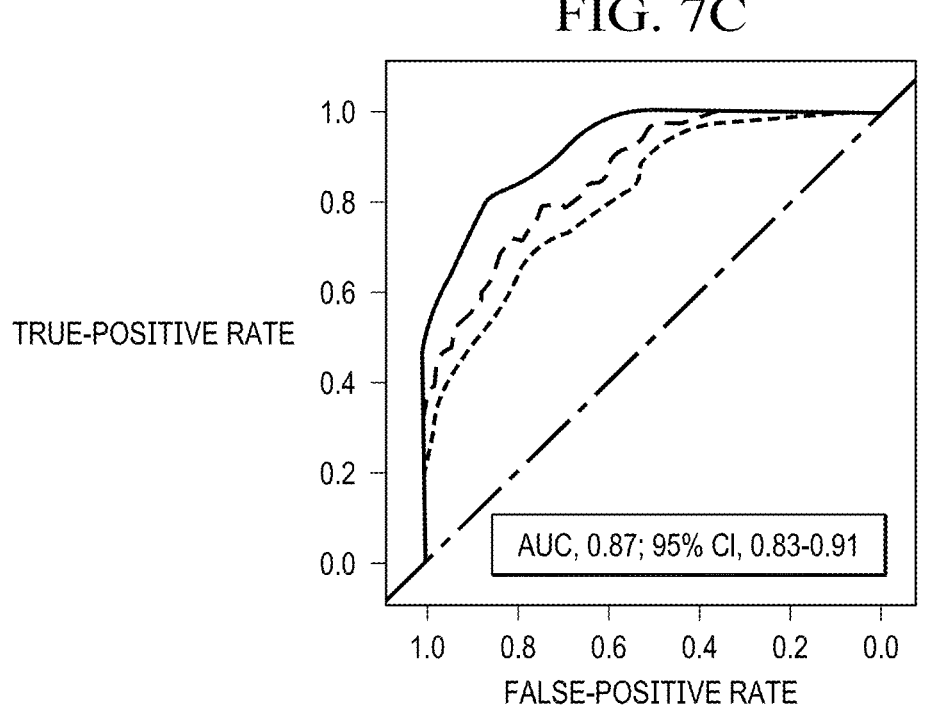
TRUE-POSITIVE RATE
AUC, 0.87; 95% CI, 0.83-0.91
FALSE-POSITIVE RATE
PRECISION-RECALL-P: 146, N: 105
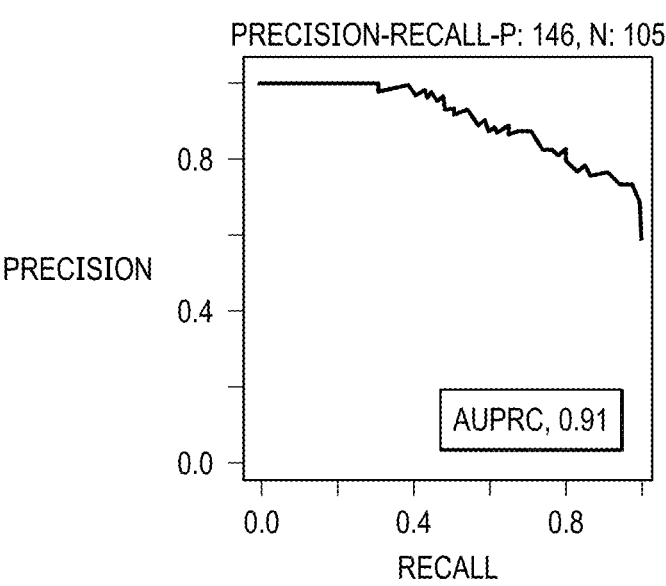
PRECISION
AUPRC, 0.91
RECALL

USING DEEP LEARNING TO PROCESS IMAGES OF THE EYE TO PREDICT VISUAL ACUITY

CROSS-REFERENCE TO RELATED APPLICATIONS

This application is a continuation of Patent Cooperation Treaty Application No. PCT/US2020/044652 filed Jul. 31, 2020, which claims the benefit of and priority to U.S. Provisional Patent Application Nos. 62/882,354 (filed on Aug. 2, 2019), 62/907,014 (filed on Sep. 27, 2019), 62/940,989 (filed on Nov. 27, 2019) and 62/990,354 (filed on Mar. 16, 2020). Each of these applications is hereby incorporated by reference in its entirety for all purposes.

BACKGROUND

Retinal diseases such as neovascular age-related macular degeneration (neovascular AMD) are characterized by pathophysiological and anatomical changes that can interfere with vision and lead to permanent vision loss. Age-related macular degeneration (AMD) is an eye disease that affects a person's vision. There are two types of AMD: dry and wet. Dry AMD is more common and is a milder form of AMD. It usually progresses gradually and slowly affects vision. Meanwhile, wet AMD, also referred to as neovascular age-related macular degeneration, is a more advanced version of AMD. One risk factor for neovascular AMD is age, where neovascular AMD typically affects people over the age of 50. Smoking also increases a person's chance of developing neovascular AMD by two to five times. Other risk factors for neovascular AMD include obesity, genetics, race, and gender. A person with a body mass index (BMI) over 30 is two and a half times more likely to develop neovascular AMD than a person with a lower BMI. Additionally, family history of neovascular AMD increases the likelihood of someone developing neovascular AMD. Females, Caucasians, and people with light-colored eyes are also at a higher risk of developing neovascular AMD. While the risk factors can provide information about the likelihood of someone developing neovascular AMD, there are no current techniques that can reliably predict disease severity and speed of degeneration.

Thus, frequently, care providers rely on frequent monitoring to determine whether to initiate and/or change a given treatment (e.g., such as intravitreal anti-vascular endothelial growth factor, which leads to improvement in vision in some subjects). One approach for objectively assessing vision capabilities is to determine which characters on an eye chart (e.g., a Snellen Eye Chart or LogMAR) were correctly identified by a person. The eye chart can include characters of different sizes (e.g., with different sizes being presented on different lines of the eye chart), and a visual acuity can be determined based on determining which size of characters were correctly identified by a viewer. When a viewer views the eye chart using glasses or contact lenses, the visual-acuity metric is typically referred to a "best corrected visual acuity".

One reason why it can be informative to monitor a corrected or best corrected visual acuity is because various vision diseases and/or vision conditions can cause changes in the eye that are not correctable via glasses or contacts. For example, excess fluid (e.g., in the macula) can cause vision blurriness that cannot be corrected via glasses or contacts. Meanwhile, many other types of vision degradation that occur naturally as a result of aging can be corrected via glasses or contacts. Thus, a corrected or best corrected visual acuity may be an indication of a disease presence, progression and/or stage.

While various eye diseases (e.g., including AMD) cause anatomical changes and further cause degradation in visual function, a precise relationship has not yet been identified that predicts current or future visual acuity based on eye anatomy. Conventional correlation analyses are limited in their ability to detect novel relationships between anatomic and visual parameters by the need to identify and prespecify a candidate set of features for analysis, a process that is limited by the insight of the human investigator. Moreover, conventional methods that prespecify features, such as central subfield thickness (CST) and central foveal thickness (CFT), typically yield aggregated measures of retinal health that may not have a sufficiently specific relationship to vision outcomes. For example, in HARBOR trial data, features derived from intraretinal fluid and total retinal thickness correlate with baseline BCVA at an $R^2=0.21$.

A desire thus exists to more reliably predict visual function based on anatomy.

BRIEF DESCRIPTION OF THE DRAWINGS

The present disclosure is described in conjunction with the appended figures:

FIG. 1. Process for predicting visual acuity of subject eye using machine-learning model.

FIG. 2. Process using visual-acuity predictions for a clinical study.

FIGS. 5A-C. Performance of deep learning algorithms that predict best-corrected visual acuity (BCVA) of <69 letters at concurrent visit from associated optical coherence tomography. (A) BCVA <69 letters. Study eye at random visit. (B) BCVA <69 letters. Fellow eye at random visit. (C) BCVA <69 letters. Both study and fellow eye at random visit.

FIGS. 6A-C. Actual versus predicted BCVA at month 12. Performance of deep learning algorithms that analyze baseline optical coherence tomography images to predict BCVA at month 12. (A) Study eyes. (B) Fellow eyes. (C) Both study and fellow eyes.

FIGS. 7A-C. Performance of deep learning algorithms that predict best-corrected visual acuity (BCVA) of <69 letters at month 12 from baseline optical coherence tomography. (A) Month 12 BCVA <69 letters. Study eyes. (B) Month 12 BCVA <69 letters. Fellow eyes. (C) Month 12 BCVA <69 letters. Both study and fellow eyes.

Figure 3:
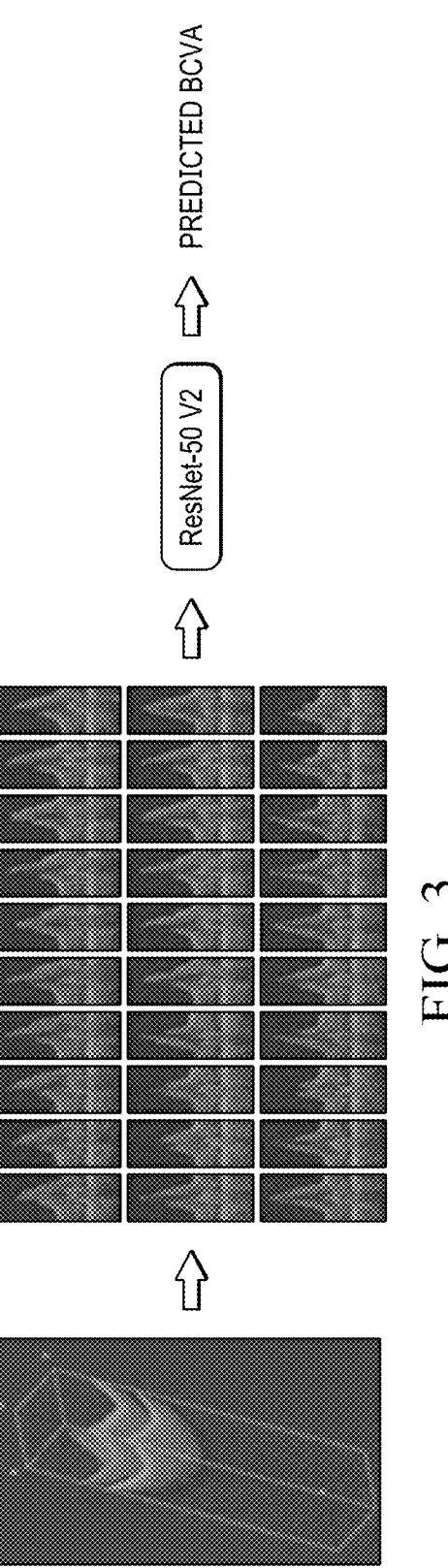
FIG. 3. Deep learning pipeline. Predicting best-corrected visual acuity (BCVA) by using three-dimensional optical coherence tomography volume represented as 30 two-dimensional images input to ResNet-50 v2 convolutional neural network.

In the appended figures, similar components and/or features can have the same reference label. Further, various components of the same type can be distinguished by following the reference label by a dash and a second label that distinguishes among the similar components. If only the first reference label is used in the specification, the description is applicable to any one of the similar components having the same first reference label irrespective of the second reference label.

DETAILED DESCRIPTION

I. Overview

This description relates to predicting a metric characterizing a visual function (e.g., visual acuity) of a subject based on an analysis of an image of an eye of the subject. The prediction may facilitate defining objectives during treatment development and selecting a treatment suited for a given individual. The image of the eye can include (for example) an optical coherence tomography (OCT) image, color fundus image or infrared fundus image. The subject may, but need not, have been diagnosed with an eye disease (e.g., macular degeneration, neovascular age-related macular degeneration, glaucoma, cataract or diabetic retinopathy).

The predicted visual acuity may include an acuity metric generated based on how accurately the subject can identify visual objects (e.g., of one or more sizes). The visual objects may include alphanumeric characters and/or the visual acuity may correspond to a capability of reading one or more alphanumeric characters on an eye chart. The predicted visual acuity may correspond to a metric corresponding to a current visual acuity (e.g., characterizing a visual acuity at a time point or within time period associated with capture of the image of the eye) or a future visual acuity (e.g., characterizing a visual acuity at a future time point or within a future time period relative to that at or within which the image of the eye was captured).

The visual acuity can be predicted (for a healthy, disease-free subject, for a subject with an eye-related disease or for a subject with an eye-related medical condition) using a trained machine learning model. In some instances, the machine learning model may be configured to output a result of a logic-based condition evaluation. For example, the machine learning model may be configured and trained to predict whether a viewer's current visual acuity or future visual acuity (e.g., at a particular time) is below a predefined threshold. The machine learning model can include (for example) a deep machine learning model, a convolutional machine learning model, a regression model, and/or a classifier model. Exemplary deep convolutional neural network architectures that may be used include AlexNet, ResNet, VGGNet, Inception, DenseNet, EfficientNet, GoogLeNet or a variation on any of these models. The machine learning model may include (for example) one or more convolutional layers, one or more pooling layers (e.g., max-pooling or average-pooling), one or more fully connected layers, one or more dropout layers and/or one or more activation functions (e.g., a sigmoid function, tanh function or rectified linear unit). The machine learning model may use one or more kernel-sized filters in the model's convolutional layers. For example, kernel sizes may vary across layers. The machine learning model may be (for example) configured and trained to output a predicted visual-acuity metric, a visual-acuity metric range (e.g., open or closed range), and/or a result based on evaluating one or more logic conditions (e.g., so as to indicate whether a subject's visual acuity is at least as good as a particular threshold).

A trained machine learning model may be defined based on a set of fixed hyperparameters (e.g., defined by a programmer or user) and a set of parameters (e.g., having values learned during training). The set of parameters can include (for example) a set of weights that nodes (or neurons) apply to transform received values. The values received by a given node can include a set of values from a previous layer (or from an input), where the set of values corresponds to a receptive field of the node (e.g., where the receptive field has a size, padding, etc. as defined by one or more hyperparameters).

In some instances, a machine learning model is trained to receive input that includes (e.g., in part or in its entirety) data corresponding to a particular time point or particular time period and to output a result that corresponds to the particular time point or particular time period. For example, the machine learning model can be trained to predict a subject's current visual acuity or visual acuity on a date on which one or more input images were initially obtained. In some instances, a machine learning model is trained to receive input that includes (e.g., in part or in its entirety) data corresponding to a particular time point or particular time period and to output a result that corresponds to a later time point or a later time period (e.g., at least 1 week from a date on which the input data was collected, at least 2 weeks from a date on which the input data was collected, at least 1 month from a date on which the input data was collected, at least 3 months from a date on which the input data was collected, at least 6 months from a date on which the input data was collected, at least 1 year from a date on which the input data was collected, at least 2 years from a date on which the input data was collected, or at least 6 years from a date on which the input data was collected).

In some instances, a machine learning model is initialized with parameters learned during training to predict a current metric (e.g., corresponding to a time or time period associated with input data) and is subsequently further trained (e.g., using transfer learning) to predict a metric for a later time point or later time period (e.g., at least 1 week from a date on which the input data was collected, at least 2 weeks from a date on which the input data was collected, at least 1 month from a date on which the input data was collected, at least 3 months from a date on which the input data was collected, at least 6 months from a date on which the input data was collected, at least 1 year from a date on which the input data was collected, at least 2 years from a date on which the input data was collected, or at least 6 years from a date on which the input data was collected). In some instances, a machine learning model is configured to receive an input value that indicates a subsequent time point for which a prediction is to be made relative to a time associated with collection of images included in the input (e.g., 3 months, 6 months, 1 year, etc.). In some instances, one or more machine learning models are separately trained so as to predict an output associated with different time points or time periods.

In some instances, a processing pipeline includes a machine learning model for processing one or more input images to generate an interim result (e.g., a prediction of a visual acuity or best corrected visual acuity associated with a current time point or time point associated with a collection of input images) and further includes one or more other machine learning models and/or one or more other post-processing functions configured to receive the interim result (e.g., representative of a predicted visual acuity at one or more first time points) and to output another result (e.g., representative of a predicted visual acuity at a second time point subsequent to the first time point). For example, another machine learning model and/or post-processing function may include regression model configured to receive the interim result and potentially one or more other variables (e.g., one or more other interim results associated with one or more other time points, one or more other subject characteristics, one or more other subject-specific eye-anatomy values, one or more variables indicative of a disease or disease state, etc.) to output a final (e.g., subject- and/or eye-specific visual-acuity metric).

One or more predicted visual acuities may be used to (for example) inform a diagnosis, prognosis, treatment selection, treatment recommendation, dosage selection and/or dosage recommendation. The one or more predicted visual acuities may be associated with a same subject, with a time point or period associated during which images of the subject's eye(s) were collected and/or a time point or period subsequent to that at which images of the subject's eye(s) were collected. In some instance, a proportional or absolute difference between an acuity predicted for a future time point and an acuity predicted for a current or previous time point is determined and used to inform a diagnosis, prognosis, clinical-trial criteria, treatment selection, treatment recommendation, dosage selection, dosage recommendation, recommended frequency of follow-ups with a medical professional, etc. A diagnosis may include (for example) identifying a disease (e.g., age-related macular degeneration), a type of a disease (e.g., neovascular age-related macular degeneration versus atrophic age-related macular degeneration) or a severity of a disease (e.g., a severity of age-related macular degeneration). A prognosis may include (for example) identifying a predicted time at which a given visual-function degradation will occur, a predicted time at which a given disease transition will occur, a probability of a given disease transition occurring (e.g., over a time period or at all), etc. For example, approximately 10-20% of subjects with atrophic AMD will transition to neovascular AMD. A predicted visual acuity associated with a future time may be used to predict whether, a probability that or a predicted time at which a subject will transition to neovascular AMD.

As one example, if a subject has been diagnosed with age-related macular degeneration, the disease may be "neo-vascular age-related macular degeneration (AMD)" (other-wise known as wet AMD) or "atrophic AMD (otherwise known as dry AMD). Approximately 80-90% of individuals with AMD have atrophic AMD. Neovascular AMD is more aggressive and accounts to about 90% of severe-vision-loss AMD cases. In some instances (e.g., when data indicates a subject has not been specifically diagnosed with neovascular or atrophic AMD), an output may predict that a subject may have neovascular AMD (instead of atrophic AMD) if a relative or absolute difference between a predicted future visual acuity and a current or recent visual acuity is above a predefined change threshold or if an absolute predicted future visual acuity is above a predefined current-time threshold. In some instances (e.g., when an initial diagnosis of atrophic AMD has been indicated or in the absence of a report of leakage of blood-vessel fluid), an output may predict that a subject may have late atrophic AMD (instead of early-stage atrophic AMD) if a relative or absolute difference between a predicted future visual acuity and a current or recent visual acuity is above a predefined change threshold or if an absolute predicted future visual acuity is above a predefined current-time threshold. In some instances (e.g., when an initial diagnosis of atrophic AMD has been indicated or in the absence of a report of leakage of blood-vessel fluid), an output may predict that a subject is at relatively high risk of transitioning to neovascular AMD (e.g., within a given time period) if a relative or absolute difference between a predicted future visual acuity and a current or recent visual acuity is above a predefined change threshold or if an absolute predicted future visual acuity is above a predefined current-time threshold.

Most subjects with atrophic AMD are not treated with medication but are instead monitored to determine whether and/or if the condition progresses to neovascular AMD. If an output predicts the subject likely has neovascular AMD, likely has late atrophic AMD and/or is at high risk of transitioning to neovascular AMD, a computing system may recommend and/or a care provider may decide to: change a schedule for image-based monitoring for the subject (e.g., such that an image of the eye is collected earlier than previously planned) and/or initiate an AMD treatment. An AMD treatment may include (for example) an anti-vascular-endothelial-growth-factor (anti-VEGF) agent (e.g., ranibi-zumab, bevacizumab, afibercept and conbercept) or farici-mab (a bispecific antibody currently in clinical studies that neutralizes angiopoietin-2 and VEGF-A).

Glaucoma is another eye disease that causes impaired vision (e.g., visual acuity). Glaucoma is caused by abnor-mally high pressure in the eye which damages the optic nerve. Risk factors for glaucoma include age, race, family history, and eye injuries. People over 60 have an increased risk of developing glaucoma. African Americans are more likely to develop glaucoma, and they are at increased risk over the age of 40. Additionally, medical conditions such as diabetes and high blood pressure can increase the risk of developing glaucoma.

Glaucoma can be diagnosed with a comprehensive eye exam. Visual acuity tests and tonometry measurements can be used to facilitate diagnosis of glaucoma. Additionally, OCT and color fundus photography can identify changes or abnormalities in the optic nerve that can indicate glaucoma.

Though it develops slowly, glaucoma could cause blind-ness over 20 years if not treated. With treatment, blindness can be prevented. In less severe cases, prescription eye drops may be used to cause the eye to produce less fluid. In more severe cases, laser surgery can be used to widen drainage networks in the eye. Imaging techniques, such as OCT and color fundus photography, can be used to monitor the development of glaucoma over time. The rate of progression may be useful in choosing a treatment option.

Other common eye conditions associated with aging that affect visual acuity are cataracts and dry eye. Cataracts are a clouding of the lens of the eye and dry eye is a lack of adequate lubrication in the eye. Cataracts can be surgically removed and dry eye can be treated with eye drops or other medications. In extreme cases, surgical measures can be taken to treat dry eye. A normal visual acuity or BCVA can be restored with treatment of both cataracts and dry eye.

Yet another eye condition that can cause reduced visual acuity is diabetic retinopathy. During the early stages of the disease, mild non-proliferative abnormalities occur, such as increased vascular permeability (which increases the flow of small molecules or even whole cells) through blood-vessel walls. During the late stages, vascular closure and/or growth of new blood vessels on the retina or vitreous posterior surface are frequently observed. Macular edema can occur at any disease stage and includes a buildup of fluid in layers of the macula due to burst blood vessels. Macular edema can result in blurry vision and reduced visual acuity.

All diabetics are at risk of developing diabetic retinopathy. Diagnosis may be made by detecting (for example) reduced visual acuity, microaneurysms (e.g., depicted in a fundus photograph or an optical coherence tomography (OCT) image), dot and blot hemorrhages (e.g., depicted in a fundus photograph or OCT image), hard retinal exudates (e.g., depicted in a fundus photograph), soft exudates (e.g., depicted in a fundus photograph), venous dilation (e.g., depicted in a fundus photograph or OCT image), venous dilation (e.g., depicted in a fundus photograph or OCT image), thickened retina (e.g., depicted in a fundus photograph or OCT image), leakage or non-perfusion of retinal and/or choroidal vasculature (e.g., as indicated through use of fundus fluorescein angiography), etc. Diabetic retinopathy is further consistent with multiple pupil-size measurements (e.g., observed after pupil dilation), such as reduced baseline pupil diameter, reduced amplitude of pupil constriction, reduced velocity of pupillary constriction and/or reduced velocity of pupillary dilation.

Early diabetic retinopathy is frequently not treated. Advanced diabetic retinopathy may be treated using anti-VEGF, vitrectomy (a surgery to remove blood and scar tissue from the eye), panretinal photocoagulation (a laser treatment to shrink blood vessels) and/or photocoagulation (a laser treatment to inhibit leakage of blood and other fluid in the eye).

Techniques disclosed herein can be used to process an image of an eye of a subject having an eye disease or eye condition (e.g., age-related macular degeneration, diabetic retinopathy, macular edema, glaucoma, cataracts or dry eye) to (for example) predict an efficacy of a particular treatment; identify a particular treatment to use or recommend and/or to facilitate design or performance of a clinical study.

II. Input Data, Preprocessing, Training Data

II.A. Input Data

Data received by a machine learning model (e.g., to be processed to generate new outputs or to be processed during training) can include one or more images of an eye of a subject of one or more processed versions thereof. The one or more images may have been captured using one or more imaging techniques, such as optical coherence tomography (OCT), color fundus photography, fundus autofluorescence or infrared fundus photography. The one or more imaging techniques may be non-invasive and/or may not require administration (e.g., intravenous or oral administration) of a dye. In other instances, the one or more imaging techniques includes a technique that includes administering a dye (e.g., as is performed for fundus fluorescein angiography).

In some instances, an input data set includes a single image. In some instances, an input data set includes a set of images, with images in the set corresponding to different depths.

II.A.1. Optical Coherence Tomography

OCT is a non-invasive imaging technique that uses light waves to construct cross-sectional images of the eye. To generate the images of the eye, an interferometer can split a low coherence near-infrared light beam towards the target tissue and a reference mirror. The backscattered light received from the target tissue and the reference mirror are combined and the interference of the signals is determined. Areas of the target tissue that reflect back more light will have a higher interference. The reflectivity information, often referred to as an A-scan, contains information about the longitudinal axis (e.g., depth) of the target tissue. The light beam can be guided in a linear direction to generate information at many lateral positions. A cross-sectional "B-scan" image can be generated from combining the depth scans at the lateral positions (e.g., using 128, 256 or 512 A-scans). The cross-sectional image can be displayed in real-time, speeding up the process of analysis and diagnosis. A three-dimensional image may be constructed to include multiple B-scans.

OCT can provide high-resolution images of an eye without contacting the eye. The OCT allows distinct layers of the retina to be studied, which may be useful in identifying diseases originating in a particular layer. Two areas of potential importance are in the retina and include the optic nerve and the macula. The optic nerve carries information from the eye to the brain, and the macula is an area with dense photoreceptor cells.

OCT can provide information about thicknesses and sizes of various layers in the eye, cellular organization and even axonal thickness. As a result, OCT can help with diagnosing and determining treatments for conditions such as neovascular AMD. OCT images that depict or are suggestive of fluid in retinal, subretinal or subpigment epithelial spaces (e.g., via dome shape reflective area in the subretinal space, an elevation of nondrusenoid retinal pigment epithelium or drusenoid pigment epithelial detachment and retinal thickening) may be consistent with presence of neovascular AMD.

II.A.2. Color Fundus Photography

Color fundus photography involves using a fundus camera or retinal camera to record color images of the interior surface of the eye. A fundus camera is a low powered microscope with a camera that can photograph the retina, retinal vasculature, optic disc, macula, and fundus of the eye. Light rays (e.g., white light) sent from the fundus camera to capture the image enter and exit through the pupil of the eye. In some instances, the pupil of the eye can be dilated to provide a larger area that can be photographed. Color fundus images depict the retina, macula, blood vessels, optic disc and the fundus.

Drusen (deposits that are predominately lipids under the retina) fluoresce and appear as white or yellow in color fundus images. Drusen is commonly detected in older adults, but the presence of large drusen and/or of a high quantity of drusen in the macula is frequently observed in AMD subjects.

II.B. Preprocessing

As indicated above, raw images may be processed to generate other images having different perspectives and/or dimensionality relative to the raw images. For example, multiple A-scans can be processed to generate one or more B-scans, and a C-scan (e.g., which may capture some three-dimensional information, such as depth) can be generated using multiple B-scans. In some instances, an image can include a three-dimensional images (e.g., generated based on multiple two-dimensional images). In some instances, color fundus photographs can be collected at different imaging angles, which may facilitate generating an image that may convey depth information.

Due to curvature of the eye, raw images may depict curved structures (e.g., curved retinal layers). A flattening technique can then be employed to flatten an image (e.g., a two-dimensional image or three-dimensional image) based on (for example) a pilot estimate of a given structure (e.g., retinal pigment epithelium). For example, an image may be filtered (e.g., with a Gaussian filter) to denoise the image, and a most intense pixel in each column of the denoised image can be identified (e.g., which may represent the retinal pigment epithelial surface). Columns may then be adjusted up or down to align the most intense pixels across the columns. As another example, the retinal pigment epithelial surface can be segmented (e.g., via an intensity thresholding), and a function (e.g., a spline function) can be fit to the segmented pixels. Columns of the image can then be realigned to flatten the spline function. In one instance, a raw image may be flattened to a retinal pigment epithelium layer segmentation, and image volumes may be cropped to pixels above and pixels below the flattened retinal pigment epithelium.

Preprocessing may include normalizing and/or standardizing intensity values, which may be performed before or after other types of preprocessing (e.g., before or after generating B-scans, generating a C-scan or applying a flattening technique).

A flattening technique and/or other pre-processing technique can be performed to align a depiction of a particular structure to a target location. For example, pixels inferred to correspond to the retinal pigment epithelial surface may be shifted (e.g., during a flattening process) to a specified row or plane, such that the same row or plane corresponds to the same structure across images.

Some machine learning models may be configured to receive images of a particular size. Thus, preprocessing may be performed to, for example, crop and/or pad an image such that its dimensions meet the particular size. Some machine learning models may be configured to receive images having a particular resolution. Thus, preprocessing may be performed to, for example, downsample or upsample an image.

II.C. Training Data

A training data set includes multiple training data elements, each being associated with a particular eye of a particular subject. Each of the multiple training data elements can further be associated with a particular time point and/or medical visit. In some instances, a given training data set corresponds to a particular type of disease. For example, a training data set may be defined to correspond to a set of subjects, who each have AMD or who each have neovascular AMD. In some instances, one or more other constraints are imposed on the subject set (e.g., such that all subjects in the subject set are within a particular age range, are not on medication, etc.).

Each of the multiple training data elements can include input data of one or more images of at least part of an eye.

In some instances, the image(s) that are to be processed by a machine-learning model are preprocessed versions of raw images (e.g., having been preprocessed using a preprocessing technique, such as one disclosed in Section II.B). In some instances, a machine-learning model includes one or more preprocessing functions (e.g., including one or more disclosed in Section II.B.) to preprocess received images.

Each of the multiple training data elements can further include a label that includes or otherwise indicates a visual acuity associated with the particular subject and associated with a particular time point, which can indicate a degree to which the subject discern visual stimuli. The visual-acuity metric may be determined by determining whether and/or a degree to which the particular subject can accurately identify and/or characterize one or more visual stimuli presented to the subject (e.g., at a particular distant from the subject and/or having one or more particular sizes). The visual-acuity metric may be specific to a particular eye of the subject by evaluating responses provided when the particular subject viewed the one or more visual stimuli with only the particular eye (e.g., and the other eye was blocked or closed).

II.C.1. Types of Visual-Acuity Metrics

The predicted visual-acuity metric can include (for example) a numeric metric, such as a ratio, a numerator (e.g., relative to a fixed denominator), a real number, an integer, etc. The predicted visual-acuity metric can include a visual-acuity category and/or visual-acuity bound. For example, a visual-acuity scale may include a set of threshold visual acuities (e.g., 20/10, 20/20, 20/25, 20/30, 20/40, 20/50, 20/70, 20/100 and 20/200 or −0.3, −0.2, −0.1, 0, 0.1, 0.2, 0.3, 0.4, 0.5, 0.6 and 0.7)—each being associated with one or more visual stimuli so as to indicate that, if a viewer can accurately identify the visual stimuli (or a characteristic thereof), the viewer has at least the associated threshold visual acuity. A predicted visual-acuity metric can be defined as a "best" across the set that corresponds to results from a particular user (e.g., indicating that the viewer could accurately identify or characterize stimuli associated with visual-acuity metric but not other stimuli associated with higher visual acuities in the set). In some instances (e.g., when using a Snellen scale), higher visual-acuity metrics represent better visual acuity relative to other metrics associated with lower visual-acuity metrics. In some instances (e.g., when using a LogMAR scale), lower visual-acuity metrics represent better visual acuity relative to other metrics associated with higher visual-acuity metrics. In some instances (e.g., when using a Jaeger scale), values along the scale do not monotonically depend on visual acuity (e.g., as J1+ represents better acuity than J1, and J1 represents better acuity than J2).

A visual-acuity metric can include a value selected from among values represented along a scale, such as Snellen scale, a LogMAR scale or a Jaeger scale. A visual-acuity metric can include a Snellen fraction, a LogMAR value or a Jaeger score. A visual-acuity metric can include a value determined based on a subject's ability to correctly identify and/or characterize one or more characters (e.g., when viewing the one or more characters with a particular eye. The one or more characters can include: one or more letters, one or more numbers, one or more tumbling E's, one or more Landolt C's and/or one or more Lea symbols presented at particular sizes and at a particular distance from the subject.

A visual-acuity metric can include a value determined based on a viewer's ability to identify and/or characterize one or more visual stimuli presented on a chart or card positioned at a particular distance (e.g., 2 meters or 4 meters) from the viewer. The chart or card can be a physical chart or card (e.g., comprising paper, plastic, laminate, cardboard, etc.) or a virtual chart or card (e.g., to be presented on a display of an electronic device. The chart or card can include multiple lines, each including one or more characters (e.g., letters, numbers, tumbling E's, Landolt C's and/or Lea symbols). Each line can be associated with a character size that indicates a size of the one or more characters (e.g., height, width and/or aspect ratio) in the line. Sizes may vary (e.g., monotonically) across lines. The quantity of lines in the chart or card can be (for example): at least 3, at least 5, at least 7, at least 9, or at least 11 lines; fewer than 20, fewer than 15, fewer than 13, fewer than 10, or fewer than 7 lines; and/or about 5, about 7, about 9 and/or about 11 lines.

The chart or card can include (for example) a Snellen chart (e.g., being taller than wide, including multiple rows of letters, each row having more characters and smaller characters than a previous line, where the inter-line character-size differences vary across the chart—both when considering absolute and relative size differences), a modified Snellen chart, a Logarithm of the Minimum Angle of Resolution (LogMAR) chart (with a same number of letters per row, letter size and inter-line spacing logarithmically varying logarithmically across lines and letters sized to a square shape), a Bailey-Lovie chart, an Early Treatment Diabetic Retinopathy Study (ETDRS) chart (with a same number of letters per row, letter size and inter-line spacing logarithmically varying logarithmically across lines and letters sized to a rectangular shape), a Rosennbaum card.

A visual-acuity metric can include a visual acuity at a particular distance (e.g., 2 meters or 4 meters), either with or without vision correction (e.g., glasses or contacts). When a visual-acuity metric is determined when a viewer is using a vision correction, the metric can include a corrected visual acuity or best corrected visual acuity.

A visual-acuity metric may include a ratio. A ratio may include a numerator that represents an estimated lower-threshold distance (in particular units) that a viewer must be relative to a visual stimulus to decipher the stimulus similarly to what an unimpaired viewer can decipher at a distance (in the particular units) as indicated in a denominator of the ratio. A ratio may include a numerator that identifies a longest distance a subject can be from a visual stimulus to accurately identify or characterize the visual stimulus (e.g., using a single eye) and may include a denominator that identifies a longest distance a representative subject (without visual impairment) can be from the visual stimulus (or a similar visual stimulus having a same or substantially similar height and/or width as the visual stimulus) to accurately identify or characterize the visual stimulus. A ratio may include a Snellen fraction. The ratio and/or testing may be defined to generate ratios having a same value for the numerator or denominator. As one example, a metric of 20/40 may indicate that the viewer must be within 20 units of measure (e.g., feet, yards, meters, etc.) from a visual stimulus to detect and/or decipher stimulus features that an average non-impaired viewer can detect and/or decipher at 40 units of measure. The ratio may include a specified numerator. For example, a model may be configured to output a ratio that includes a ratio where a numerator is set to 20.

In some instances, all of the training data elements include a same type of visual-acuity metric. For example, all of the training data elements may include a Snellen fraction. In some instances, at least two of the training data elements include different types of visual-acuity metrics. For example, a first training data element may include a Snellen fraction, and a second training data element may include a LogMAR score. In these instances, each of at least some of the training data elements may be processed to transform the visual-acuity metric. For example, a look-up table or algorithm may be used to transform a LogMAR score into a Snellen fraction, or a look-up table or algorithm may be used to transform each LogMAR score and each Snellen fraction into a score along yet another scale.

II.C.2 Timing Associations for Visual-Acuity Metrics

In some instances, for each of one or more of the training data elements, a visual-acuity metric includes one determined based on a functional assessment of a subject's eye (e.g., via answers provided in response to presentation of a chart or card) that was performed at a time corresponding to a date on which images in the training data element were collected. For example, a subject may complete a visual-acuity assessment (e.g., by attempting to correctly identify or characterize letters or other visual stimuli on an eye chart) on a same day, within a same week or within a same 2-week period as one in which images of the subject's eye(s) were collected.

In some instances, for each of one or more of the training data elements, a visual-acuity metric includes one determined based on a functional assessment of a subject's eye that was performed at a time subsequent to a date on which images in the training data element were collected. For example, a subject may complete a visual-acuity assessment at least or approximately 1 month, at least or approximately 2 months, at least or approximately 6 months, at least or approximately 1 year, at least or approximately 2 years or at least or approximately 5 years after a date on which or time period during which images of the subject's eye(s) were collected.

In some instances, for each of one or more of the training data elements, the training data element includes a visual-acuity metric associated with a time corresponding to a date on which images in the training data element were collected and further includes another visual-acuity metric associated with a time subsequent to a date on which images in the training data element were collected.

III. Machine Learning Models

Training data may be used to train a machine learning model, such that a set of parameters are learned. The trained machine learning model can then be used to process other input (e.g., of a type described in Section II.A, which may be preprocessed using a type such as one disclosed in Section II.B) to generate an output predicting a visual acuity.

III.A. Model Architecture

A machine learning model may have (for example) a deep learning architecture, a residual-network architecture and/or a convolutional neural network architecture. A deep learning architecture can be configured such that the model performs hierarchical learning, to initially identify low-level features at one or more lower levels and to identify higher level features at higher levels. A machine learning model may have (for example) a ResNet architecture, an AlexNet architecture, a DenseNet architecture, EfficientNet architecture, a GoogLeNet architecture or a VGGNet architecture.

A machine learning model may include one or more convolution layers (e.g., at least 3 convolution layers, at least 4 convolution layers, at least 5 convolution layers or at least 7 convolution layers), one or more sparse convolution layers, one or more pooling layers (e.g., a max pooling layer or average pooling layer), one or more inception modules, use of dropout, use of batch normalization, one or more dense layers and/or one or more activation functions. In some instances, each of one or more or all convolution layers are followed by a pooling layer. For example, a model may include 5 convolution layers, and each of 3 of the convolution layers may be followed by a pooling layer. The pooling layer(s) can reduce a number of parameters that are to be learned by the model.

A machine learning model may include a residual layers or skip connections that feed output from one layer (layer l) to another layer not immediately adjacent to the one layer (layer l+2, layer l+3, layer l+4, etc.). The skips can reduce or avoid vanishing-gradient situations. Thus, skips can further facilitate use of networks having a large number of layers. A machine learning model may include (for example) at least 10, at least 20, at least 30, at least 40 or at least 45 convolutional layers (e.g., potentially in addition to one or more max-pooling layers, one or more average-pooling layers and/or one or more fully connected layers). A machine learning model can include residual blocks that each include 3 layers. Sizes of kernels used in residual blocks in earlier stages of the model may be smaller than sizes of kernels used in residual blocks in later stages of the model.

A machine learning model can be configured to output a numeric output or a categorical output (e.g., indicating a level of visual acuity and/or including a binary prediction as to whether a visual acuity is equal to or better than a threshold). In some instances, a machine learning model that outputs a numeric output includes a linear activation function and/or uses an error-based loss function (e.g., mean squared error). A machine learning model that outputs a categorical output may include (for example) a softmax activation function and/or may use a categorical loss function (e.g., a sparse categorical cross-entropy loss function).

III.B. Model Training

In some instances, a first set of training data includes a first set of training data elements, each including one or more images (of an eye of a subject) and a label corresponding to a visual acuity of the subject at a time corresponding to a time at which the image(s) were captured. A machine learning model having a particular architecture can be trained using the first set of training data such that a first set of parameters is learned.

A second set of training data can include a second set of training data elements, each including one or more images (of an eye of a subject) and a label corresponding to a visual acuity of the subject at a time subsequent later than (e.g., 12 months later than) a time at which the image(s) were captured. In some instances, each subject represented in the first set of training data is also represented in the second set of training data. In some instances, at least some of the subjects represented in the first set of training data are also represented in the second set of training data. In some instances, subjects represented in the first set of training data are at least partly or entirely different than subjects represented in the second set of training data.

A machine learning model having an architecture that is at least partly or entirely the same as the particular architecture can be trained using the second set of training data such that a second set of parameters is learned. For example, each of the models trained using the first and second training data sets may include a ResNet-50 CNN architecture.

In some instances, a model that is to be trained to predict a subsequent visual-acuity metric is initialized using parameters learned by a model trained to predict current (e.g., corresponding to a same time period during which input images were collected) visual acuity. Subsequent training may thereafter be performed.

In some instances, a single machine learning model may be trained using both the first and second training data sets, but the machine learning model may be configured to receive (in addition to an image) an indication as to which time point a prediction is to correspond.

In some instances, a machine learning model may be configured to predict a rate of decline of visual acuity, one or more rate constants, etc. to predict how visual acuity will change in time (e.g., how quickly acuity will decline) for the subject's eye. A prediction may include a constant to be used (for example) in a linear, logarithmic, polynomial and/or exponential function to characterize visual acuity across time.

IV. Use of Model Outputs to Inform Clinical-Study Design, Prognosis and Treatment Selection A model output that predicts a current visual-acuity metric, predicts a visual-acuity metric at a particular future time point and/or that predicts how visual acuity will change may be used to (for example) inform clinical-trial design, subject prognosis and selection of a treatment.

IV.A. Clinical-Study Design

In some instances, a clinical study may be defined such that an eligibility criterion relates to an observed or predicted visual acuity. For example, the clinical study may be defined to enroll subjects who have visual acuity equal to or worse than 20/80 vision (and who meet other eligibility criteria). An acuity-based eligibility criteria may be defined to relate to a visual-acuity metric characterizing a current or past visual acuity and having been generated based on an image of at least part of a subject eye. The criterion may require the predicted metric or to accept either the predicted metric or an observed metric. An acuity-based eligibility criteria may alternatively or additionally be defined to relate to a predicted visual-acuity metric characterizing a predicted visual acuity at a subsequent time (e.g., requiring a predicted visual acuity at a time point of a year from a current time to be worse than 20/40 vision).

Many clinical studies (e.g., clinical trials) are controlled, such that a first group of subjects receives an investigatory treatment and a second group of subjects receives a different treatment, control treatment, no treatment and/or standard of care. Model results that correspond to a predicted visual acuity may be used to facilitate selecting subject groups such that a population of subjects in a first group are similar to a population of subjects in a second group. Currently, there is substantial variability across AMD subjects as to how quickly visual function will decline. Thus, two AMD subjects having identical visual acuity at one time may have markedly different visual function at a second time. This may result in inadvertently defining subject groups in a manner such that one group would have progressed much more quickly than the other group, which could confound results.

Thus, stratification for a clinical study may be designed to include an eligibility criterion that specifies a range of predicted visual acuities at a future time point. For example, a clinical study may require that OCT images or a color fundus image were collected within a first time period (before the trial begins) and that a predicted acuity at a second time point (e.g., 12 months or 18 months from the first time period) be within a predefined range. A criteria may further identify a constraint (e.g., range) for a predicted acuity corresponding to a time at which the image(s) were collected.

Additionally or alternative, predicted visual acuities may be used to process clinical-trial data and to develop indications and/or hypotheses as to what type of subjects may be particularly likely (or alternatively, particularly unlikely) to benefit from a given treatment. For example, during a trial or after completion of a trial, for each subject in a treatment group, a current metric may be determined, such as a current visual acuity (e.g., as determined using eye charts or cards), predicted current visual acuity (e.g., as determined using a current image of an eye), current diagnosis of AMD (e.g., whether the AMD is wet or dry AMD), etc. It could then be determined whether a predicted visual-acuity metric corresponding to a pre-trial time (e.g., associated with a time period during which the images were taken) or another predicted visual-acuity metric corresponding to a subsequent time was predictive of the current metric.

IV.B. Prognosis

Predicted visual-acuity metrics may be used as part of or to inform a prognosis identified for a subject. A subject may have a poorer prognosis when it is predicted that a visual acuity of the subject at a subsequent time (e.g., in 12 months) is worse than a threshold or corresponds to a substantial degradation as compared to a subject with a predicted subsequent visual acuity that is better than the threshold or corresponds to less substantial diagnosis. A prognosis may influence subject outlook, treatment selection, etc.

IV.C. Treatment Selection

There is substantial variability with regard to the degree to which different subjects respond to a given treatment. For example, antivascular endothelial growth factor (anti-VEGF) is a standard of care for neovascular AMD. However, there is high variability across subjects with regard to a degree to which the subjects respond.

Disease activity may be present when (for example) visual acuity declines or does not improve, a central retinal thickness as observed by OCT does not decrease, new intraretinal fluid is detected, new subretinal fluid is detected, and/or new retinal thickening is detected. A predicted future visual acuity may thus inform whether a given subject will effectively respond to a particular treatment. For example, a model may be trained using a training data set that includes images of subjects' eyes before treatment is administered and that includes (as labels) a predicted visual acuity (or predicted change in visual acuity) at a subsequent time, while the subject receives a particular treatment between a first time period (associated with image collection) and a second time point (associated with the subsequent visual acuity).

Thus, a care provider may be able to predict a degree to which visual acuity will change while using a particular treatment. Multiple models may even be used to assess different potential treatments. The care provider may then be able to predict whether a particular treatment will be effective for a particular subject and/or which of multiple treatments will be most effective for a particular subject.

For example, with respect to neovascular AMD, one treatment option is anti-VEGF injections (where VEGF stands for a protein called vascular endothelial growth factor, which can promote formation of new blood vessels in the back of the eye, which can lead to macular degeneration due to leakage of blood and other fluids). Anti-VEGF injections are injections into the vitreous of the eye to stop the abnormal growth of blood vessels. The most common anti-VEGF injections are ranibizumab, bevacizumab, conbercept and aflibercept. A person's response to anti-VEGF injections is frequently monitored by manual assessment of OCT or color fundus photography to determine how often the injections should be received.

Anti-VEGF injections may be received monthly until it is decided that the interval between injections can be extended. Vision loss due to neovascular AMD is frequently, but not always, halted with the use of anti-VEGF injections. Occasionally, subjects regain some lost vision as a result of anti-VEGF injections.

Another treatment option (currently under Phase-III investigations) is a port delivery system (PDS) used in conjunction with anti-VEGF medications. The PDS is a permanent refillable eye implant that can continuously deliver the anti-VEGF medication to the eye over a period of months. The PDS can allow a subject to visit their ophthalmologist only twice a year for medication refills. Decreasing the number of required visits to the ophthalmologist can reduce the burden of treatment that often leads to under-treatment and inferior visual outcomes.

Yet another treatment option is faricimab, which is an antibody under Phase-III investigations. Faricimab is administered intraoccularly. Some lost vision may be regained in response to the treatment.

Further yet, another treatment option for neovascular AMD is photodynamic therapy (PDT). PDT is a laser treatment that breaks down the extra blood vessels. A doctor may opt for PDT instead of anti-VEGF injections if the vision loss experienced by the subject is gradual instead of sudden. In some cases, PDT can be combined with anti-VEGF treatments to slow down central vision damage caused by neovascular AMD.

Thus, model predictions may be used to inform a decision whether to recommend or use (for example) an anti-VEGF agent, an anti-VEGF agent that is delivered via intraocular injection, a particular VEGF agent (e.g., ranibizumab or bevacizumab), a PDS or PDT for a particular subject and/or subject eye.

IV.D. Treatment Initiation and/or Monitoring Change

In some instances, a machine-learning model output may be used to recommend use, prescribe or administer an AMD treatment to a subject who would not otherwise take the AMD treatment or possibly any AMD treatment at the time. For example, a subject may have a diagnosis of atrophic AMD, which is frequently not treated with medication. However, an output from a machine-learning model (e.g., trained using data corresponding to subjects diagnosed with atrophic AMD, subjects diagnosed with neovascular AMD or both) may correspond to a prediction that a visual acuity (e.g., best corrected visual acuity) corresponding to a baseline day (during which an input image was collected), corresponding to a concurrent visit or corresponding to a subsequent time (e.g., 3 days, 5 days, 1 week, 2 weeks, 1 month, 6 months, 1 year, 2 years, 5 years from the baseline day) will be worse than a predefined threshold (e.g., corresponding to a Snellen fraction of 20/30, 20/40, 20/60 or 20/80). Alternatively or additionally, an output from a machine-learning model (e.g., trained using data corresponding to subjects diagnosed with atrophic AMD, subjects diagnosed with neovascular AMD or both) may correspond to a prediction that a visual acuity will decrease by at least a threshold fractional or absolute predefined amount (e.g., corresponding to a Snellen fraction at a subsequent time being less than 90%, less than 75%, less than 66% or less than 50% that at a baseline time).

In response to one or more of these types of predictions, a computing system (e.g., that generated the prediction(s) or one that receive the prediction(s) from another computing system) may output a recommendation of a particular action, a care provider (e.g., physician, nurse, doctor's office, hospital, etc.) may provide a recommendation of a particular action and/or a particular action may be performed. The particular action may include (for example) changing a diagnosis of the subject (e.g., from atrophic AMD to neovascular AMD, or from early atrophic AMD to late atrophic AMD), initiating an AMD treatment for the subject (e.g., that includes one or more treatments identified herein), changing a treatment schedule for the subject (e.g., increasing a frequency of anti-VEGF administrations) and/or changing the subject's AMD treatment (e.g., to one identified herein). For example, the particular action may include initiating anti-VEGF treatment for the subject. In some instances, the particular action includes changing a monitoring plan, such that (for example) a next date of a imaging of an eye of the subject or of a visual-acuity test is scheduled or changed (e.g., to an earlier date), a frequency of imaging an eye of the subject is increased and/or a frequency of testing the subject's vision is increased.

V. Exemplary Processes

FIG. 1 depicts a process 100 for predicting visual acuity of subject eye using machine-learning model. Process 100 begins at block 105 where a machine-learning model is trained to learn a set of parameters using a set of training images and a set of labels. Each of the set of training images may depict at least part of an eye of a training subject, such that the set of training images depict at least part of each of an eye of each of the set of training subjects. The set of training images may include (for example) one or more color fundus photographs, one or more OCT images and/or one or more other images. Each of the set of labels may include (for example) a visual-acuity metric, such as a numeric visual acuity, an identification of a visual-acuity range, and/or an indication as to whether the eye of the training subject has a visual acuity that is below a particular threshold. The visual-acuity metric may characterize a visual acuity of the eye of the training subject at a time that the training image was collected (e.g., on a same day at which the image was collected) or at a time after the training image was collected (e.g., approximately 6 months, approximately 12 months, approximately 2 years or approximately 5 years after the date on which the training image was collected).

In some instances, each of the set of training subjects had been (e.g., prior to collection of their training image) diagnosed with a vision disease or vision medical condition, such as macular degeneration, age-related macular degeneration, neovascular macular degeneration, glaucoma, diabetic retinopathy, cataracts, or macular edema. In some instances, each of one or more or each of all of the set of training subjects had not been diagnosed with a vision disease or vision medical condition. In some instances, the set of training subject includes both training subjects with a vision disease or vision condition and training subjects without a vision disease or vision condition.

The machine-learning model can include a model disclosed herein, such as a deep convolutional neural network. The machine-learning model can include one or more residual connections and/or one or more feedforward layers.

The set of parameters may include a set of weights and/or one or more convolutional kernels.

The machine-learning model may further include one or more pre-processing functions, which may pre-process an image and then send the pre-processed image to (for example) a neural network. The machine-learning model may further include one or more post-processing functions, which may (for example) transform an output from the neural network to another result. For example, a post-processing function may transform a result to a particular visual-acuity scale or may identify a range within which a numeric neural-network output resides.

At block 110, an image of at least part of an eye of a particular subject is accessed. The particular subject may be different than each subject in the set of training subjects and/or may have been one of the set of training subjects. The image accessed at block 110 may include a fundus photograph, a color fundus photograph, an OCT image or another image. The image can include a digital image. The at least part of the eye can include (for example) at least part of: the retina, macula, optic disc, lens, pupil and/or iris. For example, an image may depict at least part of the retina and at least part of the macula.

At block 115, the image of the at least part of the eye of the particular subject is input into the trained machine-learning model. The trained machine-learning model can determine, based on the image, a visual-acuity metric corresponding to a predicted visual acuity of the eye. The predicted visual acuity may include (for example) a numeric visual acuity, a categorical visual acuity, a visual-acuity range and/or an indication as to whether a predicted visual acuity exceeds a threshold.

At block 120, the visual-acuity metric is returned. For example, the visual-acuity metric may be presented (e.g., displayed) via a user interface. As another example, the visual-acuity metric may be transmitted to another device (e.g., from a server to a user device).

FIG. 2 depicts a process 200 using visual-acuity predictions for a clinical study. At block 205, the visual acuity of each subject of a set of subjects is predicted. The visual acuity can include a visual acuity of an eye of the subject. The visual acuity that is predicted can include a visual-acuity metric predicted based on an image of at least part of the eye of the subject. The visual acuity can be predicted using a method herein, such as all of part of process 100. The predicted visual acuity may be a visual acuity predicted for a time corresponding to capture of the image or a subsequent time. The predicted visual acuity may be a visual acuity predicted for a particular time corresponding to the clinical study (e.g., 6 months after a treatment is initiated, 12 months after a monitoring begins, etc.).

At block 210, for each of the set of subjects, it can be determined whether the subject is eligible to participate in a particular clinical study. The determination can be based on whether each of a set of eligibility is satisfied for the subject. A given criterion may include logic, such that (for example) it is satisfied if any of multiple conditions are satisfied.

The set of criteria may indicate that the subject is to be within a particular age, is to have been diagnosed with a particular vision disease or condition (e.g., age-related macular degeneration, neovascular age-related macular degeneration), does not have one or more particular other diseases, etc. In some instances, the set of subjects include subjects enrolled in the clinical study.

The set of criteria may include a criterion using the predicted visual acuity for the subject. For example, the criterion may indicate that the subject is to be associated with a predicted visual-acuity metric above a predefined threshold. As another example, the criterion may indicate that the subject is to be associated with a visual-acuity-metric change that is above a predefined threshold. A visual-acuity-metric change can include an absolute or relative difference between a visual-acuity metric associated with a time point relative to a visual-acuity metric associated with a baseline time point. The time point may include (for example) a current time, a time a predefined duration after initiation of treatment (e.g., 6 months after treatment initiation, 12 months after treatment initiation), a time a predefined duration after initiation of a clinical study, a particular date, etc. The baseline time point may correspond to (for example) a time before a clinical study or treatment of the subject eye began, a time at which the clinical study or treatment of the subject eye began, etc. In some instances, each of the visual-acuity metric associated with the time point and the visual-acuity metric associated with the time point and the visual-acuity metric associated with the baseline time point include a visual-acuity metric generated based on processing of at least part of an image of the subject eye (e.g., using a machine-learning model). For example, an image of at least part of the subject eye collected at the baseline time point may be used to generate a predicted visual-acuity metric for the subject eye at the baseline time point and also a visual-acuity metric for the subject eye at the subsequent time point. As another example, an image of at least part of the subject eye may be collected at each of the baseline time point and subsequent time point, and the images can be processed to generate respect predicted visual-acuity metrics. In some instances, one of the visual-acuity metric associated with the time point and the visual-acuity metric associated with the time point and the visual-acuity metric associated with the baseline time point is generated based on a visual-acuity test (e.g., using an eye chart or eye card), and the other of the visual-acuity metric associated with the time point and the visual-acuity metric associated with the time point and the visual-acuity metric associated with the baseline time point is generated by processing of at least part of an image of the subject eye.

At block 215, the clinical study is conducted with a subset of the set of subjects, where each subject in the subset was determined to be eligible to participate in the clinical study. It may be determined, for each subject in the subset, that the criterion related to visual acuity was satisfied. Conducting the clinical study may include (for example) stratifying the subset of subjects into two arms and providing an investigational treatment to subjects in one arm. Subjects in the other arm may receive (for example) a different treatment, no treatment, a different dosage of the investigational treatment, a different type of administration or formulation of the investigational treatment, standard of care, etc.

At block 220, a result of the clinical study is generated. For example, a result may indicate an extent to which the investigational treatment was effective at slowing, stopping or reversing a given medical condition (e.g., as indicated via a vision test, imaging of an eye or other test). The efficacy may be estimated by comparing vision or other medical metrics between the first and second subsets, between subjects receiving the given treatment and subjects not receiving the given treatment, etc. In some instances, a result indicates a degree to which observed visual acuities of subjects having received treatment for a period of time compared to visual acuities of the subjects based on processing of images of at least part of the subjects' eyes collected at a baseline time.

VI. Examples

VI.A. Machine Learning Model for Processing OCT Images to Predict Visual-Acuity Metrics The present Example assessed whether deep learning can automatically predict concurrent and future BCVA from OCT images from subjects with neovascular AMD in the phase 3 HARBOR clinical study (NCT00891735, referred to herein as "HARBOR"). Specifically, results related to: (1) models that assess the quality of a deep learning model to predict exact best-corrected visual acuity (BCVA) values from OCT images, and (2) models that predict BCVA of <69 letters (Snellen equivalent, 20/40), <59 letters (Snellen equivalent, 20/60), or ≤38 letters (Snellen equivalent, 20/200) from OCT IMAGEs. For BCVA outcomes, deep learning models were evaluated for their ability to predict BCVA from an OCT image taken at the same (concurrent) visit, and for their ability to predict month 12 BCVA from baseline OCT image. Snellen equivalents of 20/40 and 20/60 were chosen because visual acuity worse than these levels are considered to reflect visual acuity impairment based on the United States and World Health Organization definitions, respectively. A Snellen equivalent of 20/200 or worse was used to reflect the definition of legal blindness in the United States.

VI.A.1. Methods

VI.A.1.a. Sources of Data

Prospectively collected BCVA measurements and OCT images taken of 1071 subjects from the phase 3 HARBOR clinical study were used. HARBOR adhered to the tenets of the Declaration of Helsinki and was Health Insurance Portability and Accountability Act compliant. The protocol was approved by each institutional review board before study start and all subjects provided written informed consent for future medical research and analyses based on results of the trial.

The HARBOR study enrolled 1097 adult subjects with treatment-naïve subfoveal choroidal neovascularization (CNV) secondary to neovascular AMD who had BCVA between 20/40 and 20/320 (Snellen equivalent) using standard ETDRS charts and protocols. Subjects (one study eye each) were randomized 1:1:1:1 to ranibizumab given according to one of the following treatment regimens: 0.5 mg monthly, 0.5 mg as needed (PRN), 2.0 mg monthly, and 2.0 mg PRN. Subjects in the PRN groups received three monthly injections followed by monthly evaluations, with retreatment only if there was any sign of disease activity on OCT image or if there was a ≥5-letter decrease in BCVA from the previous visit. BCVA measurements and OCT images were obtained at baseline and at monthly intervals for 24 months.

OCT images. Images were collected using the spectral-domain Cirrus HD-OCT IMAGE instrument (Carl Zeiss Meditec, Dublin, CA, USA). Resolution was 200×200×1024 voxels with a size of 30.0×30.0×2.0 μm, covering a volume of 6×6×2 mm. The dataset consisted of 50,275 OCT IMAGE scans from 1071 subjects. For each of the 50,275 OCT IMAGE scans, the retina was flattened to the retinal pigment epithelium layer segmentation provided by Zeiss software, and the volumes were cropped to 384 pixels above and 128 pixels below the flattened retinal pigment epithelium. Thirty slices of 512×200 pixels were generated per scan by rotating about the z axis at angles of 0, 30, 60, 90, 120, and 150 degrees in reference to the center of the cropped volume, offset at −8, −4, 0, 4, and 8 pixels for each of the six angles, resulting in a total of 1,508,250 slices. The OCT IMAGE dataset was split at the subject-level into (1) a randomly selected internal validation test set of 147 subjects to be used for evaluation (Table 1), and (2) a set of 924 subjects that was further split into five folds to be used for model development via cross-validation (Table 2). The subjects in each fold remained constant for each outcome variable.

TABLE 1

Characteristics of the Internal Validation Test Set used
to Evaluate the Models to Predict BCVA from OCT IMAGE.

| Characteristic | Study Eyes | Fellow Eyes | All Eyes |
|---|---|---|---|
| No. of subjects with OCT IMAGE | 147 | 147 | 147 |
| No. of OCT IMAGEs with BCVA | 3616 | 3610 | 7226 |
| No. of images | 108480 | 108300 | 216780 |
| BCVA, mean (±SD) | | | |
| Baseline | 53.93 (13.20) | 69.46 (22.92) | 61.66 (20.20) |
| Month 6 | 64.74 (15.05) | 70.60 (22.55) | 67.65 (19.33) |
| Month 12 | 63.87 (16.96) | 69.49 (23.15) | 66.69 (20.46) |
| Month 18 | 63.19 (17.81) | 69.98 (21.73) | 66.58 (20.12) |
| Month 24 | 65.02 (17.12) | 68.56 (22.56) | 66.78 (20.06) |
| All time points* | 63.24 (15.98) | 69.88 (22.40) | 66.56 (19.73) |
| Mean of all visits | 62.68 (14.92) | 69.49 (22.42) | 66.08 (19.31) |
| BCVA range | | | |
| Baseline | 55 (19, 74) | 93 (0, 93) | 93 (0, 93) |
| Month 6 | 83 (10, 93) | 98 (0, 98) | 98 (0, 98) |
| Month 12 | 89 (0, 89) | 100 (0, 100) | 100 (0, 100) |
| Month 18 | 82 (8, 90) | 96 (0, 96) | 96 (0, 96) |
| Month 24 | 78 (12, 90) | 98 (0, 98) | 98 (0, 98) |
| All time points* | 93 (0, 93) | 100 (0, 100) | 100 (0, 100) |
| Mean of all visits | 72.97 (13.23, 86.20) | 95.40 (0.04, 95.44) | 95.40 (0.04, 95.44) |
| No. of subjects with OCT IMAGE at baseline and BCVA at month 12 | 126 | 125 | 126 |
| No. of baseline images from subjects with baseline OCT IMAGE and BCVA at month 12 | 3780 | 3750 | 7530 |

BCVA, best-corrected visual acuity; OCT IMAGE, optical coherence tomography; SD, standard deviation.
*BCVA from screening through month 24.

TABLE 2

Characteristics of the OCT IMAGE Dataset to Develop the
Deep Learning Models to Predict BCVA from OCT IMAGE.

| Characteristic | Study Eyes | Fellow Eyes | All Eyes |
|---|---|---|---|
| No. of subjects with OCT IMAGE | 924 | 919 | 924 |
| No. of OCT IMAGEs with BCVA | 21623 | 21426 | 43049 |
| No. of images | 648690 | 642780 | 1291470 |
| BCVA, mean (±SD) | | | |
| Baseline | 54.18 (12.73) | 67.22 (23.33) | 60.65 (19.85) |
| Month 6 | 62.89 (15.92) | 70.26 (21.30) | 66.55 (19.14) |
| Month 12 | 63.92 (16.87) | 69.72 (22.30) | 66.81 (19.97) |
| Month 18 | 63.49 (17.31) | 69.85 (21.68) | 66.66 (19.86) |
| Month 24 | 63.12 (17.97) | 68.93 (22.18) | 66.01 (20.38) |
| All time points* | 62.39 (16.29) | 69.49 (22.01) | 65.92 (19.68) |
| Mean of all visits | 61.68 (15.00) | 68.34 (22.35) | 65.00 (19.31) |

TABLE 2-continued

Characteristics of the OCT IMAGE Dataset to Develop the
Deep Learning Models to Predict BCVA from OCT IMAGE.

| Characteristic | Study Eyes | Fellow Eyes | All Eyes |
|---|---|---|---|
| BCVA range | | | |
| Baseline | 75 (3, 78) | 97 (0, 97) | 97 (0, 97) |
| Month 6 | 88 (6, 94) | 99 (0, 99) | 99 (0, 99) |
| Month 12 | 93 (2, 95) | 100 (0, 100) | 100 (0, 100) |
| Month 18 | 89 (6, 95) | 100 (0, 100) | 100 (0, 100) |
| Month 24 | 96 (0, 96) | 100 (0, 100) | 100 (0, 100) |
| All time points* | 99 (0, 99) | 100 (0, 100) | 100 (0, 100) |
| Mean of all visits | 81.03 (9.93, 90.96) | 97.59 (0, 97.59) | 97.59 (0, 97.59) |
| No. of subjects with OCT IMAGE at baseline and BCVA at month 12 | 720 | 708 | 722 |
| No. of baseline images from subjects with baseline OCT IMAGE and BCVA at month 12 | 21600 | 21240 | 42840 |

BCVA, best-corrected visual acuity; OCT IMAGE, optical coherence tomography; SD, standard deviation.
*BCVA from screening through month 24.

VI.A.1.b. Outcome Variables for Deep learning Modeling

BCVA. The BCVA outcomes of interest were (1) BCVA in ETDRS letters at each study visit, and (2) whether a specific BCVA value was <69 letters (Snellen equivalent, 20/40), <59 letters (Snellen equivalent, 20/60), or ≤38 letters (Snellen equivalent, 20/200). Snellen equivalents of 20/40 and 20/60 were chosen because they are considered to reflect functionally meaningful levels of visual acuity impairment, and a Snellen equivalent of 20/200 or worse was used to reflect the definition of legal blindness in the United States.

Mean (±standard deviation [SD]) BCVA of the study eyes in the internal validation test set was 53.93 (±13.20) letters at baseline and 65.02 (±17.12) letters at month 24; mean (±SD) BCVA of the fellow eyes was 69.46 (±22.92) letters at baseline and 68.56 (±22.56) letters at month 24 (Table 1). The range of visual acuity in the study eyes at baseline, month 6, month 12, month 18, and month 24 was 55, 83, 89, 82, and 78 letters, respectively (Table 1). The range of visual acuity in the fellow eyes at baseline, month 6, month 12, month 18, and month 24 was 93, 98, 100, 96, and 98 letters, respectively (Table 1).

VI.A.1.c. Deep learning Algorithms

DL models were evaluated for their ability to predict (1) exact BCVA value in ETDRS letters from OCT images obtained on the same visit; (2) exact BCVA at month 12 from baseline OCT IMAGE; (3) BCVA <69 letters (Snellen equivalent, 20/40), <59 letters (Snellen equivalent, 20/60), or ≤38 letters (Snellen equivalent, 20/200) from OCT images obtained on the same visit; and (4) BCVA <69, <59, or ≤38 letters at month 12 from a baseline OCT IMAGE. Predicting BCVA at Concurrent Visit.

Deep learning modeling was performed using TensorFlow (1.14.0) with Keras (2.2.5) on a Nvidia V100 GPU, and the ResNet-50 v2 CNN architecture. Individual slices of 512× 200 pixels were randomly shuffled from the training set and fed into the CNN using a batch size of 64 images. The model was trained to predict BCVA at the same visit as the OCT IMAGE scan (FIG. 3). In some instances, layers of global average pooling and dropout (0.85) were added to the CNN using L2 regularization (0.05) on the final dense layer with a linear activation function. This model is referred to in this Example as the "concurrent visit regression model". The loss function was mean squared error and the optimizer was RAdam. The model was trained for only one epoch for each cross-validation fold.

In some instances, the concurrent visit regression model architecture was used, except the final layer used a softmax activation function with a sparse categorical cross-entropy loss function. Models were initialized with the weights from the regression model for each fold. Models were trained for two epochs with the base model layers untrainable using Adam optimizer, then an additional one epoch with the base model layers trainable using stochastic gradient descent (SGD) optimizer.

Predicting BCVA at 12 Months From Baseline. For the regression task predicting BCVA at month 12 from baseline OCT images, deep learning modeling was performed using TensorFlow (1.14.0) with Keras (2.2.5) on a Nvidia V100 GPU, and the ResNet-50 v2 CNN architecture. Individual slices of 512×200 pixels were randomly shuffled from the training set and fed into the CNN using a batch size of 64 images. The model was trained to predict BCVA at the same visit as the OCT IMAGE scan (FIG. 3). In some instances, layers of global average pooling and dropout (0.995) were added to the CNN using L2 regularization (0.05) on the final dense layer with a linear activation function. For each fold, models were initialized with the weights from the regression model trained to predict BCVA at the concurrent visit. The first three epochs were trained using SGD optimizer with the base model layers untrainable, then trained for an additional 1000 epochs with the base model layers trainable using SGD optimizer. This model is referred to in this Example as the "12 month regression model".

For classification, the 12 month regression model architecture was used, except the final layer used a softmax activation function with a sparse categorical cross-entropy loss function. For each fold, models were initialized with the weights from the regression model trained to predict BCVA at 12 months from baseline. Models were trained for 20 epochs with the base model layers untrainable using RAdam optimizer. The weights used to predict were chosen from the epoch with the lowest validation loss in each fold.
Evaluation of the Deep Learning Models.

Metrics to evaluate the model fits at a particular visit were calculated at the eye-level by the average of the predictions per eye generated for the 30 slices from each of the five development models on the out-of-sample internal validation test set. In other words, each of the five cross-validation models that have seen 80% of the data from the training set are used to generate a prediction for each of the 30 slices per eye in the test set, resulting in 150 predictions per eye, of which the mean of the 150 predictions is taken. Furthermore, to evaluate model performance at the concurrent visit across all of the visits while accounting for the potential bias of repeated measurements of the same eye, the mean of all visits were determined for the regression task, and a visit was randomly selected for each subject in the classification task. The $R^2$ value, root-mean-square error (RMSE), and mean difference (MD) and 95% limits of agreement (LOA) from Bland-Altman plots were used to evaluate the deep learning regression models, whereas the area under the receiver operating characteristic curve (AUC) and the area under the precision-recall curve (AUPRC) were used to assess the performance of the deep learning models for classification. To understand if the deep learning prediction of month 12 BCVA from baseline OCT IMAGE contributed additional information compared with using baseline BCVA alone, linear models were fit using the R statistical programming language to predict BCVA at month 12 from (i) a univariable input of the deep learning prediction of month 12 BCVA from baseline OCT IMAGE, (ii) a univariable input of baseline BCVA, and (iii) a multivariable input of both the deep learning prediction of month 12 BCVA from baseline OCT IMAGE and baseline BCVA. Additionally, results from the five-fold cross-validation tuning set are reported using the mean of the 30 tuning predictions per eye per visit (Tables 3-6).

VI.A.2. Results

VI.A.2.a. Predicting Best-Corrected Visual Acuity (BCVA) at Concurrent Visit

Figure 4A:
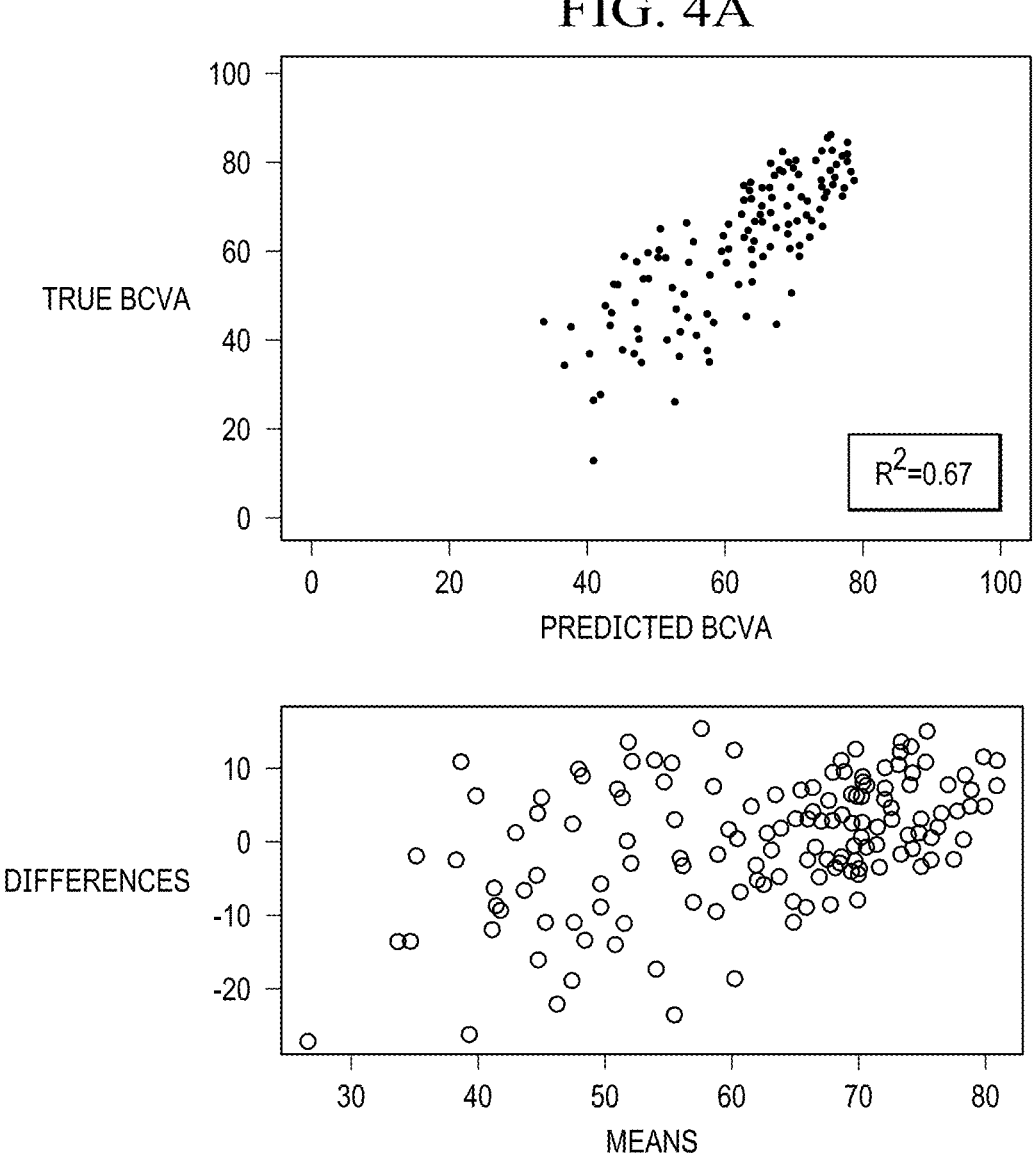
FIGS. 4A-C. Actual versus predicted best-corrected visual acuity (BCVA) at the concurrent visit. Performance of deep learning algorithms that analyze optical coherence tomography images to predict BCVA for concurrent visit. (A) Study eye mean over all visits. (B) Fellow eye mean over at all visits. (C) Both study and fellow eye mean over all visits.
Figure 4B:
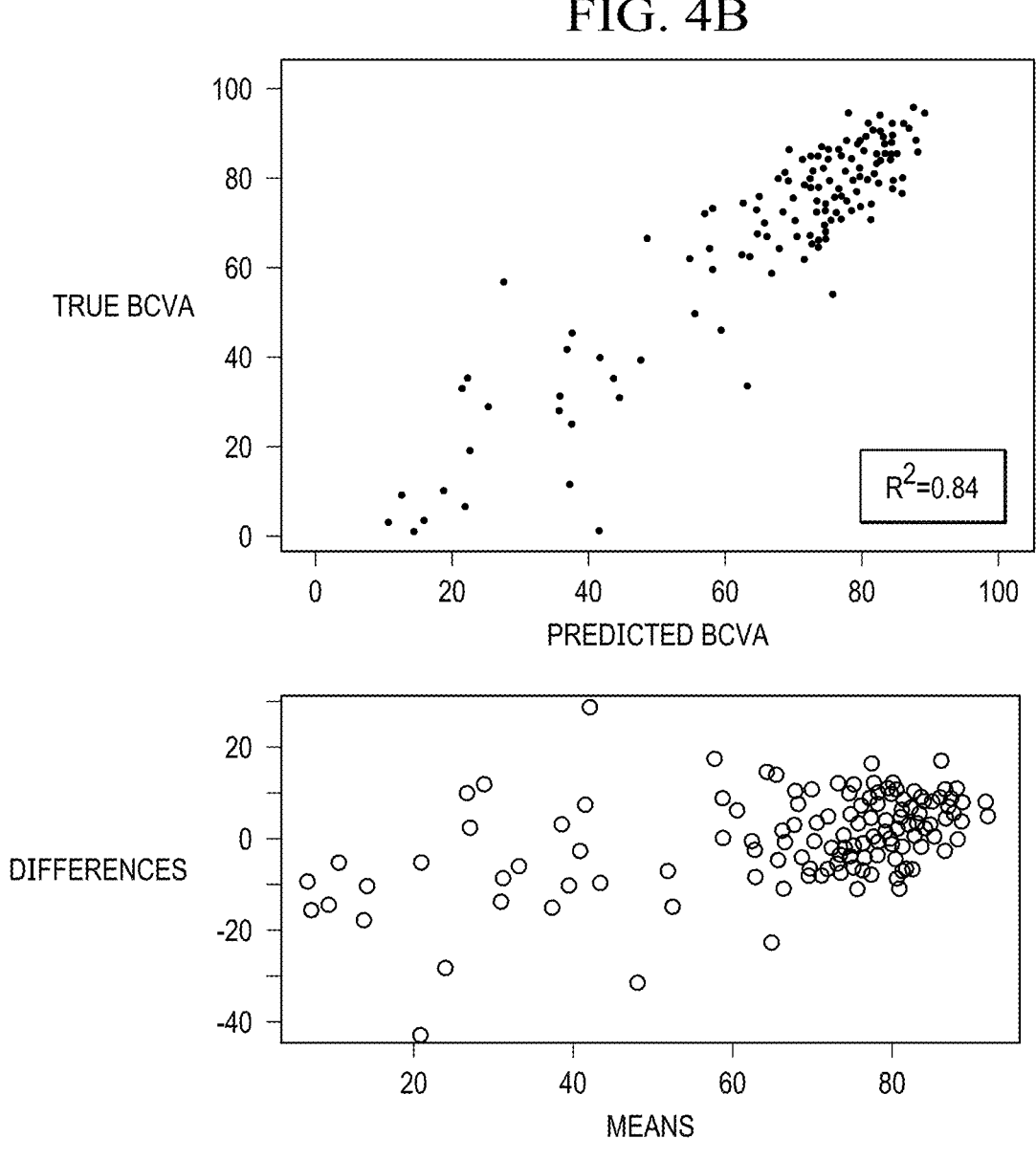
Figure 4C:
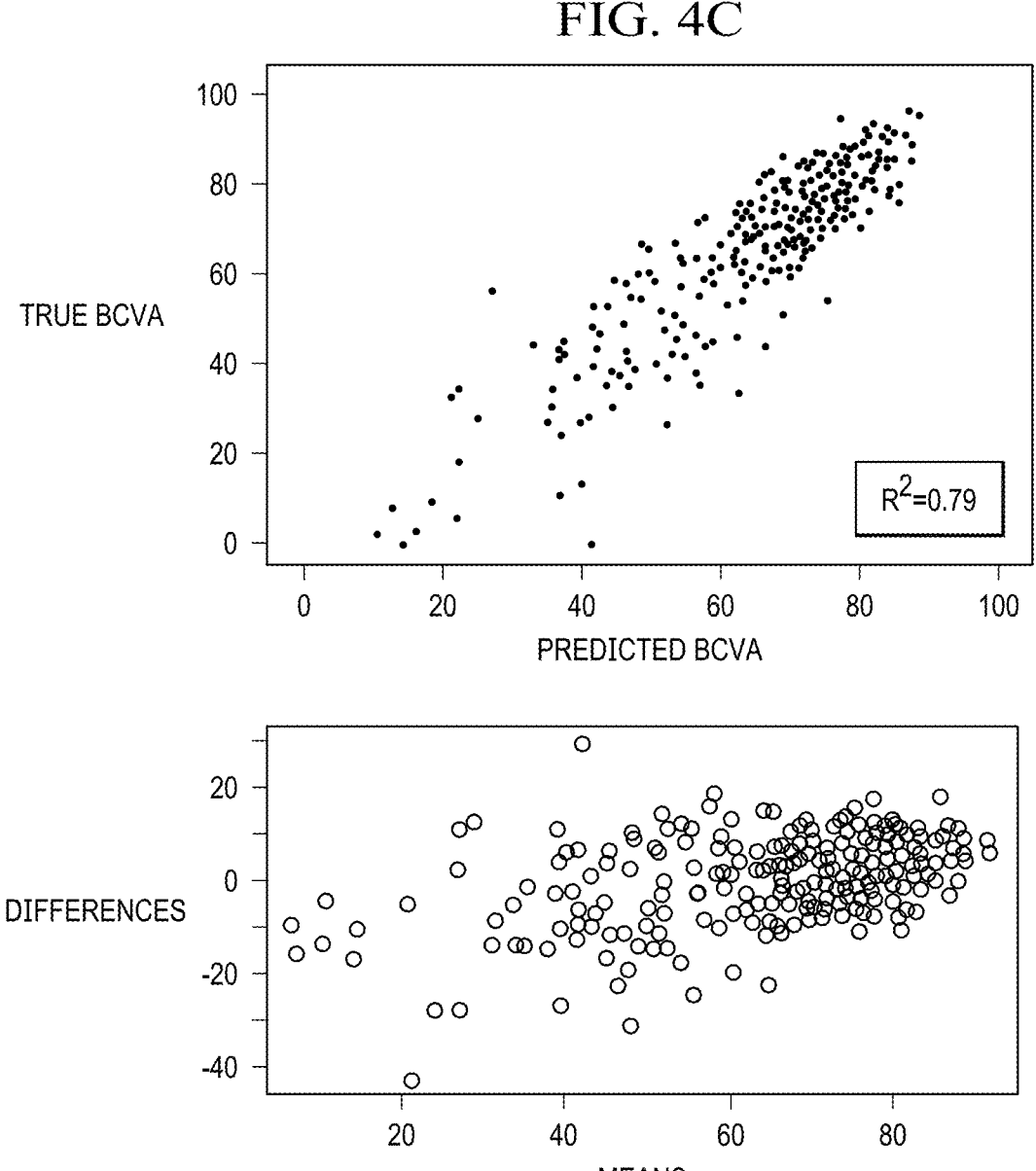

Regression Results. In the study eyes, the deep learning model to predict BCVA at concurrent visit had an $R^2=0.24$, RMSE=11.55, MD=−1.81 letters, 95% LOA, −26.57 to 22.95 letters at baseline, and an $R^2=0.67$, RMSE=8.60, MD=0.04 letters, 95% LOA, 16.96 to 17.04 letters for the mean over all of the visits (Table 3; FIG. 4A). In the fellow eyes, $R^2=0.80$, RMSE=10.35, MD=−1.86 letters, 95% LOA, −23.03 to 19.31 letters at baseline, and $R^2=0.84$, RMSE=9.01, MD=0.51 letters, 95% LOA, −17.58 to 18.61 letters for the mean over all of the visits (Table 3; FIG. 4B). In all eyes, $R^2=0.66$, RMSE=11.75, MD=−1.84 letters, 95% LOA, −24.83 to 21.16 letters at baseline, and $R^2=0.79$, RMSE=8.78, MD=0.28 letters, 95% LOA, −17.26 to 17.81 letters for the mean over all of the visits (Table 3; FIG. 4C).

TABLE 3

Performance of the Deep learning Model for Regression of BCVA on OCT Image

| | Regression of BCVA on OCT IMAGE | | | | | | | | | | | |
|---|---|---|---|---|---|---|---|---|---|---|---|---|
| | Study Eyes | | | | Fellow Eyes | | | | All Eyes | | | |
| | $R^2$ | CI | RMSE | No. | $R^2$ | CI | RMSE | No. | $R^2$ | CI | RMSE | No. |
| Baseline | 0.24 | 0.12, 0.37 | 11.55 | 126 | 0.80 | 0.72, 0.85 | 10.35 | 125 | 0.66 | 0.59, 0.73 | 11.75 | 251 |
| Month 6 | 0.54 | 0.42, 0.65 | 10.22 | 136 | 0.80 | 0.73, 0.85 | 10.14 | 134 | 0.72 | 0.66, 0.78 | 10.18 | 270 |
| Month 12 | 0.62 | 0.51, 0.71 | 10.46 | 142 | 0.82 | 0.75, 0.86 | 9.95 | 143 | 0.75 | 0.70, 0.80 | 10.18 | 285 |
| Month 18 | 0.63 | 0.52, 0.72 | 10.85 | 138 | 0.80 | 0.74, 0.86 | 9.67 | 138 | 0.74 | 0.68, 0.79 | 10.25 | 276 |
| Month 24 | 0.62 | 0.51, 0.72 | 10.54 | 133 | 0.79 | 0.72, 0.85 | 10.38 | 132 | 0.73 | 0.67, 0.78 | 10.42 | 265 |
| All time points | 0.55 | 0.53, 0.57 | 10.70 | 3616 | 0.79 | 0.77, 0.80 | 10.37 | 3610 | 0.71 | 0.70, 0.73 | 10.55 | 7226 |
| Mean of all visits | 0.67 | 0.57, 0.75 | 8.60 | 147 | 0.84 | 0.78, 0.88 | 9.01 | 147 | 0.79 | 0.75, 0.83 | 8.78 | 294 |

BCVA, best-corrected visual acuity;
OCT IMAGE, optical coherence tomography;
CI, 95% confidence interval;
RMSE, root mean square error.

TABLE 4

Performance of the Deep Learning Models for Binary Classification of BCVA <69 Letters (Snellen Equivalent, 20/40), <59 Letters (Snellen Equivalent, 20/60), and ≤38 Letters (Snellen Equivalent, 20/200) at Concurrent Visit From Associated Optical Coherence Tomography.

| Predicted BCVA From Concurrent OCT | Study Eyes | | | Fellow Eyes | | | All Eyes | | |
|---|---|---|---|---|---|---|---|---|---|
| IMAGE | AUC | CI | No. | AUC | CI | No. | AUC | CI | No. |
| <69 letters | 0.89 | 0.83, 0.94 | 147 | 0.93 | 0.89, 0.98 | 147 | 0.92 | 0.89, 0.95 | 294 |
| <59 letters | 0.92 | 0.87, 0.97 | 147 | 0.97 | 0.94, 1.00 | 147 | 0.95 | 0.92, 0.97 | 294 |
| ≤38 letters | 0.92 | 0.87, 0.96 | 147 | 0.98 | 0.96, 1.00 | 147 | 0.96 | 0.93, 0.98 | 294 |

AUC, area under the receiver operating characteristic curve;
BCVA, best-corrected visual acuity;
OCT IMAGE, optical coherence tomography;
CI, 95% confidence interval.

TABLE 5

Cross-validation Results. Performance of Linear Model for
Regression of BCVA at Month 12 From Baseline OCT and Baseline Letters.

| | Linear Regression of Month 12 BCVA From Baseline OCT and Baseline BCVA | | | | | | | | | | | |
| --- | --- | --- | --- | --- | --- | --- | --- | --- | --- | --- | --- | --- |
| | Study Eyes | | | | Fellow Eyes | | | | All Eyes | | | |
| | $R^2$ | CI | RMSE | No. | $R^2$ | CI | RMSE | No. | $R^2$ | CI | RMSE | No. |
| Baseline OCT | 0.36* | 0.30, 0.41 | 13.43 | 720 | 0.73* | 0.69, 0.76 | 11.27 | 708 | 0.57* | 0.54, 0.61 | 12.73 | 1428 |
| Baseline BCVA | 0.34* | 0.28, 0.39 | 13.61 | 720 | 0.83* | 0.81, 0.86 | 8.79 | 708 | 0.64* | 0.60, 0.66 | 11.79 | 1428 |
| Baseline OCT + baseline BCVA | 0.45** | 0.39, 0.50 | 12.44 | 720 | 0.85** | 0.81, 0.87 | 8.48 | 708 | 0.67** | 0.64, 0.70 | 11.17 | 1428 |

BCVA, best corrected visual acuity; OCT,
optical coherence tomography;
CI, 95% confidence interval;
RMSE, root-mean-square error;
*P < 0.001 for univariable model compared to null hypothesis;
**P < 0.001 for each coefficient in multivariable model.

TABLE 6

Cross-validation Results. Performance of the Deep Learning Models for Binary Classification of
Month 12 BCVA <69 Letters (Snellen Equivalent, 20/40), <59 Letters (Snellen Equivalent, 20/60),
and ≤38 Letters (Snellen Equivalent, 20/200) From Baseline OCT.

| Predicted BCVA at Month | Study Eyes | | | Fellow Eyes | | | All Eyes | | |
| --- | --- | --- | --- | --- | --- | --- | --- | --- | --- |
| 12 From Baseline OCT | AUC | CI | No. | AUC | CI | No. | AUC | CI | No. |
| <69 letters at month 12 | 0.78 | 0.75, 0.81 | 720 | 0.89 | 0.86, 0.92 | 708 | 0.86 | 0.84, 0.88 | 1428 |
| <59 letters at month 12 | 0.80 | 0.77, 0.84 | 720 | 0.94 | 0.92, 0.97 | 708 | 0.89 | 0.87, 0.91 | 1428 |
| ≤38 letters at month 12 | 0.85 | 0.80, 0.89 | 720 | 0.97 | 0.95, 0.99 | 708 | 0.93 | 0.91, 0.95 | 1428 |

AUC, area under the receiver operating characteristic curve;
BCVA, best-corrected visual acuity;
OCT, optical coherence tomography;
CI, 95% confidence interval.

Classification Model Predicting BCVA <69 Letters (Snellen Equivalent, 20/40).

In the study eyes, the deep learning model to predict BCVA of <69 letters (Snellen equivalent, 20/40) had an AUC=0.89 for one concurrent visit randomly taken per eye, and an AUPRC=0.88 with a class balance of 72 positive eyes and 75 negative eyes. (Table 4; FIG. 5A). In the fellow eyes, the deep learning model to predict BCVA of <69 letters (Snellen equivalent, 20/40) had an AUC=0.93 for one concurrent visit randomly taken per eye, and an AUPRC=0.97 with a class balance of 103 positive eyes and 44 negative eyes. (Table 4; FIG. 5B). In all eyes, the deep learning model to predict BCVA of <69 letters (Snellen equivalent, 20/40) had an AUC=0.92 for one concurrent visit randomly taken per eye, and an AUPRC=0.94 with a class balance of 175 positive eyes and 119 negative eyes. (Table 4; FIG. 5C).
Classification Model Predicting BCVA <59 Letters (Snellen Equivalent, 20/60).

In the study eyes, the deep learning model to predict BCVA <59 letters had an AUC=0.92 for one concurrent visit randomly taken per eye, and an AUPRC=0.95 with a class balance of 100 positive eyes and 47 negative eyes. (Table 4). In the fellow eyes, the deep learning model to predict BCVA <59 letters had an AUC=0.97 for one concurrent visit randomly taken per eye, and an AUPRC=0.99 with a class balance of 114 positive eyes and 33 negative eyes. (Table 4). In all eyes, the deep learning model to predict BCVA <59 letters had an AUC=0.95 for one concurrent visit randomly taken per eye, and an AUPRC=0.98 with a class balance of 214 positive eyes and 80 negative eyes. (Table 4).
Classification Model Predicting BCVA of ≤38 Letters (Snellen Equivalent, 20/200).

In the study eyes, the deep learning model to predict BCVA of ≤38 letters had an AUC=0.92 for one concurrent visit randomly taken per eye, and an AUPRC=0.99 with a class balance of 113 positive eyes and 14 negative eyes. (Table 4). In the fellow eyes, the deep learning model to predict BCVA of ≤38 letters had an AUC=0.98 for one concurrent visit randomly taken per eye, and an AUPRC=1.00 with a class balance of 129 positive eyes and 18 negative eyes. (Table 4). In all eyes, the deep learning model to predict BCVA of ≤38 letters had an AUC=0.96 for one concurrent visit randomly taken per eye, and an AUPRC=0.99 with a class balance of 262 positive eyes and 32 negative eyes. (Table 4).
VI.A.2.b. Predicting BCVA at 12 Months from Baseline OCT Image
Regression Results.

Figure 6A:
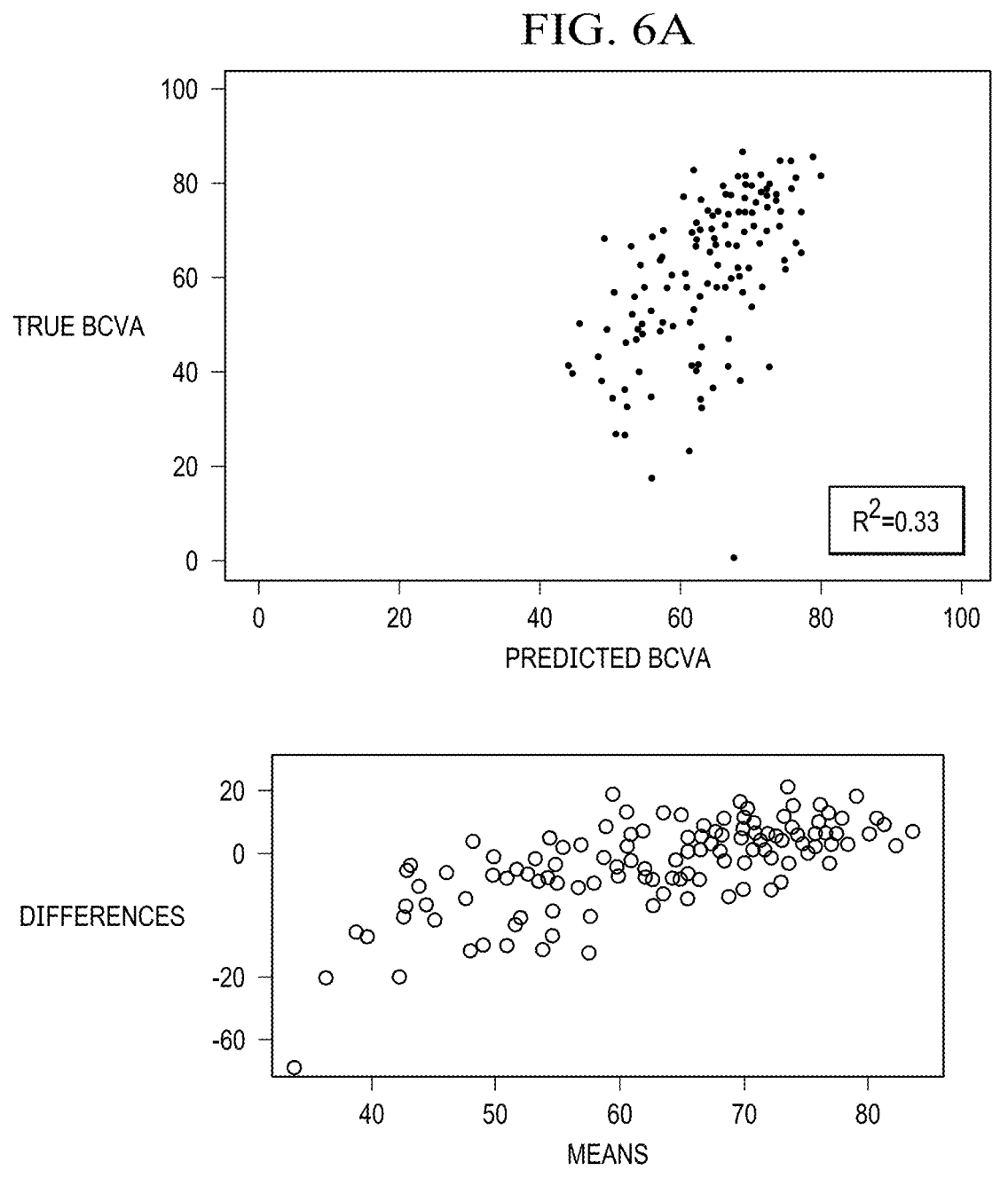
Figure 6B:
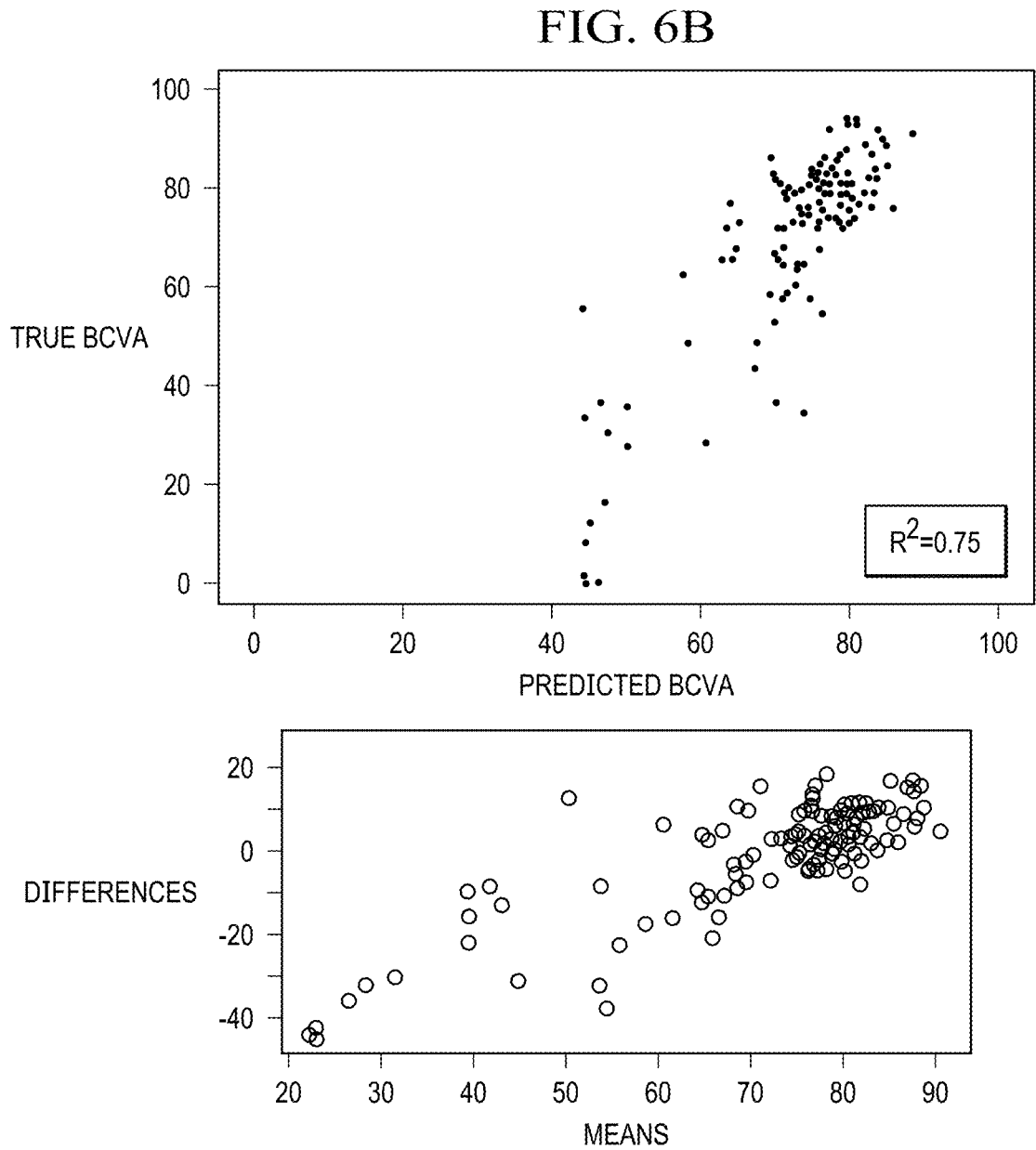
Figure 6C:
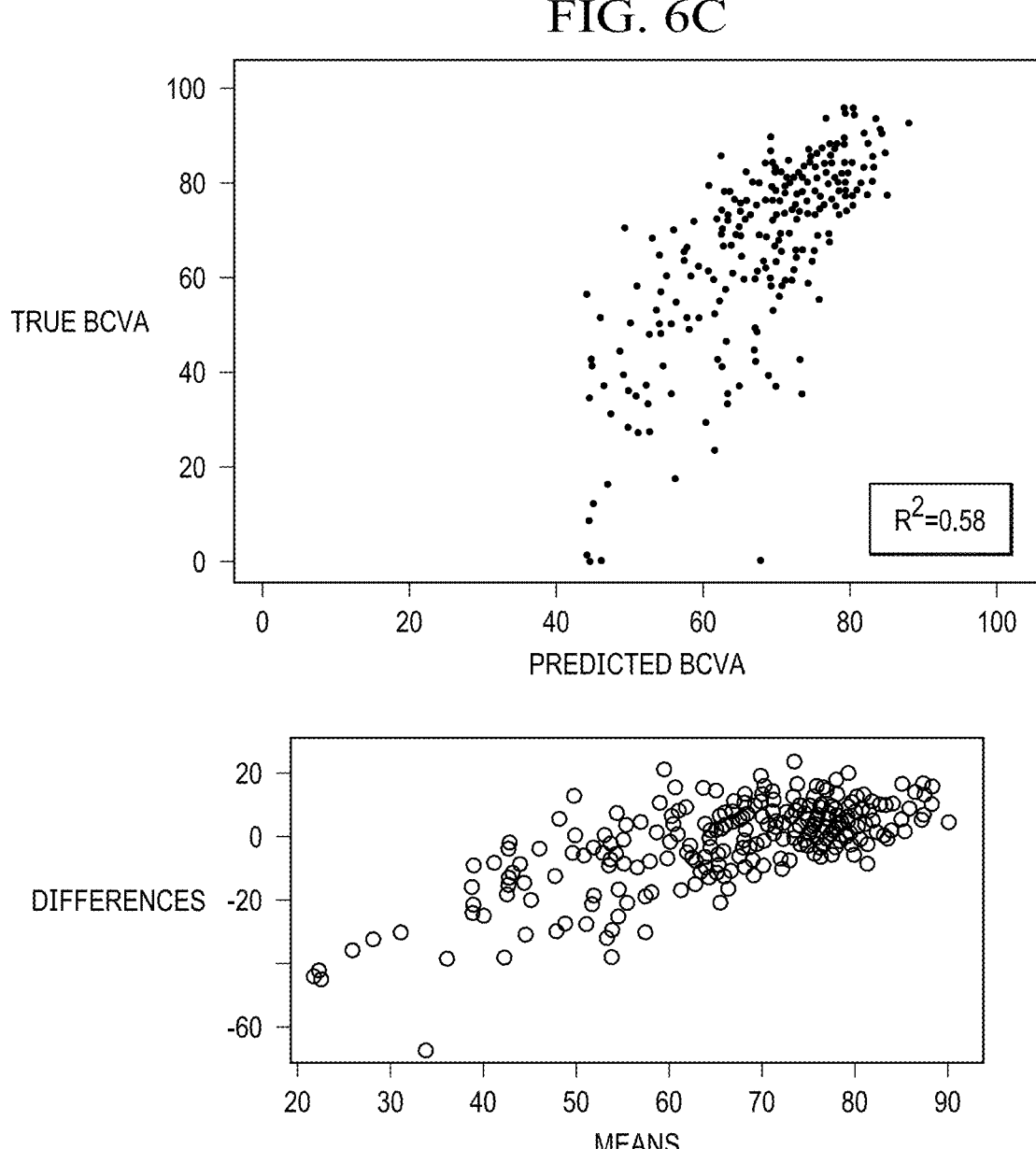

The characteristics of the dataset used to evaluate the ability of the model to predict month 12 BCVA from baseline OCT IMAGE are shown in Table 1. The deep learning model to predict BCVA at 12 months from baseline OCT IMAGE had an $R^2$=0.33, 0.75, and 0.58, and an RMSE=14.16, 11.27, and 13.25 for study eyes, fellow eyes, and all eyes, respectively (Table 7; FIG. 6A, 6B, 6C). The deep learning model to predict BCVA at 12 months from baseline OCT IMAGE had an MD=−1.63 letters, 95% LOA, −29.48 to 26.22 letters for study eyes, an MD=−2.31 letters, 95% LOA, −29.96 to 25.33 letters for fellow eyes, and an MD=−1.97 letters, 95% LOA, −29.67 to 25.73 letters for all eyes (FIG. 6A, 6B, 6C). The multivariable linear model to predict BCVA at 12 months from both deep learning predictions of month 12 BCVA from baseline OCT IMAGE and baseline BCVA had an $R^2$=0.40, 0.88, and 0.68 for study eyes, fellow eyes, and all eyes, respectively (Table 7). Classification Model Predicting BCVA <69 Letters (Snellen Equivalent, 20/40).

Figure 7B:
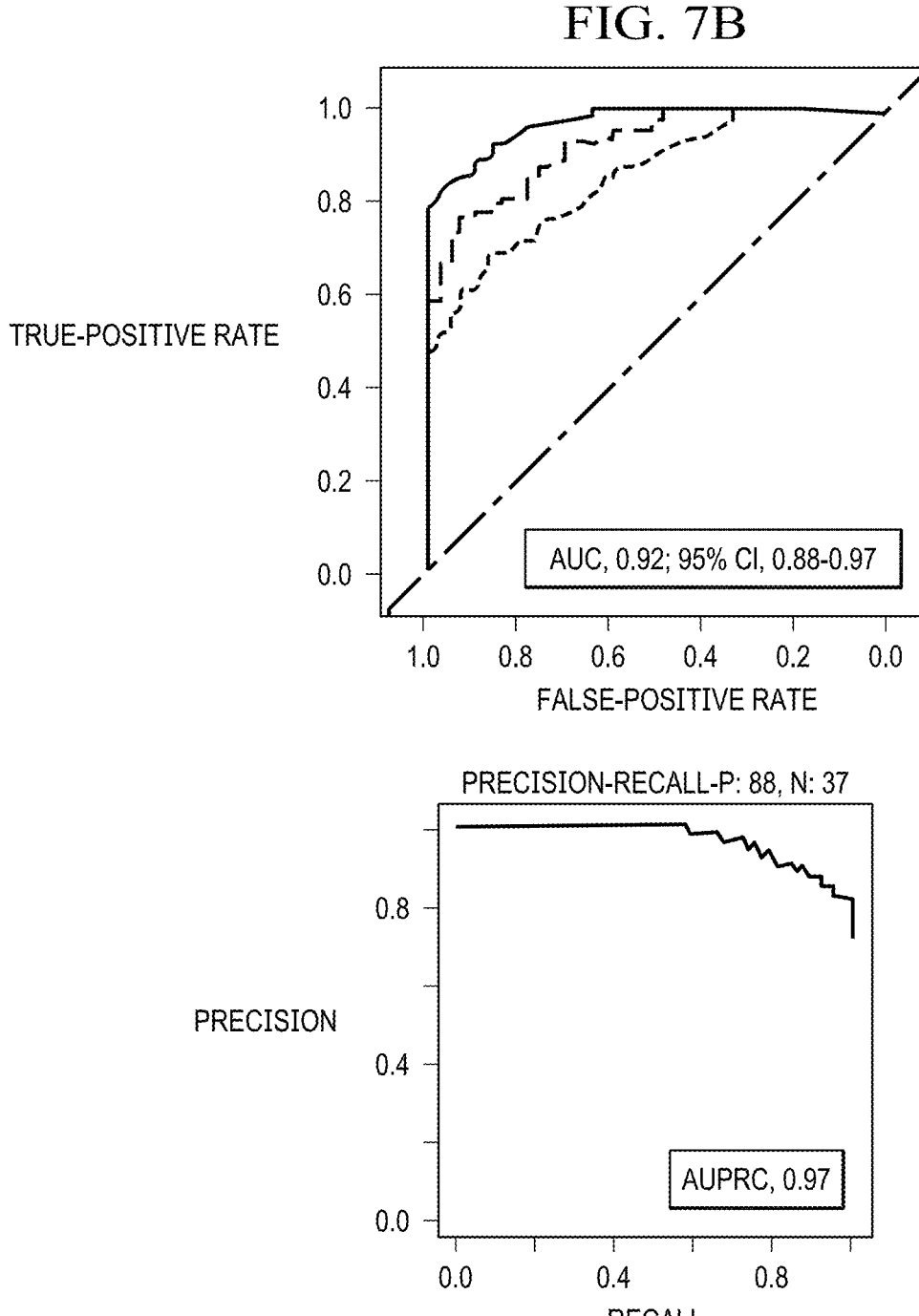

The deep learning model to predict month 12 BCVA of <69 letters from baseline OCT IMAGE had an AUC=0.80, 0.92, and 0.87 for study eyes, fellow eyes, and all eyes, respectively (Table 8; FIG. 7A, 7B, 7C). In study eyes, the deep learning model to predict month 12 BCVA of <69 letters from baseline OCT IMAGE had an AUPRC=0.74 with a class balance of 58 positive eyes and 68 negative eyes. In fellow eyes, the deep learning model to predict month 12 BCVA of <69 letters from baseline OCT IMAGE had an AUPRC=0.97 with a class balance of 88 positive eyes and 37 negative eyes. In all eyes, the deep learning model to predict month 12 BCVA of <69 letters from baseline OCT IMAGE had an AUPRC=0.91 with a class balance of 146 positive eyes and 105 negative eyes.
Classification Model Predicting BCVA <59 Letters (Snellen Equivalent, 20/60).

The deep learning model to predict month 12 BCVA <59 letters from baseline OCT IMAGE had an AUC=0.84, 0.93, and 0.89, for study eyes, fellow eyes, and all eyes, respectively (Table 8). In study eyes, the deep learning model to predict month 12 BCVA of <59 letters from baseline OCT IMAGE had an AUPRC=0.90 with a class balance of 83 positive eyes and 43 negative eyes. In fellow eyes, the deep learning model to predict month 12 BCVA of <59 letters from baseline OCT IMAGE had an AUPRC=0.98 with a class balance of 101 positive eyes and 24 negative eyes. In all eyes, the deep learning model to predict month 12 BCVA of <59 letters from baseline OCT IMAGE had an AUPRC=0.95 with a class balance of 184 positive eyes and 67 negative eyes.

TABLE 7

Performance of Linear Model for Regression of BCVA at Month 12 From
Baseline OCT Image and Baseline Letters Linear Regression of Month 12 BCVA From Baseline OCT IMAGE and Baseline BCVA

|  | Study Eyes | | | | Fellow Eyes | | | | All Eyes | | | |
|---|---|---|---|---|---|---|---|---|---|---|---|---|
|  | $R^2$ | CI | RMSE | No. | $R^2$ | CI | RMSE | No. | $R^2$ | CI | RMSE | No. |
| Baseline OCT IMAGE | 0.33* | 0.20, 0.47 | 14.16 | 126 | 0.75* | 0.62, 0.82 | 11.27 | 125 | 0.58* | 0.49, 0.65 | 13.25 | 251 |
| Baseline BCVA | 0.25* | 0.13, 0.39 | 14.98 | 126 | 0.87* | 0.82, 0.91 | 8.04 | 125 | 0.62* | 0.54, 0.69 | 12.49 | 251 |
| Baseline OCT IMAGE + baseline BCVA | 0.40** | 0.24, 0.54 | 13.45 | 126 | 0.88** | 0.81, 0.93 | 7.70 | 125 | 0.68** | 0.57, 0.75 | 11.61 | 251 |

BCVA, best-corrected visual acuity;

OCT IMAGE, optical coherence tomography;

CI, 95% confidence interval;

*P < 0.001 for univariable model compared to null hypothesis;

**P < 0.001 for each coefficient in multivariable model.

45

TABLE 8

Performance of the Deep Learning Models for Binary Classification of Month 12 BCVA <69
Letters (Snellen Equivalent, 20/40), <59 Letters (Snellen Equivalent, 20/60),
and ≤38 Letters (Snellen Equivalent, 20/200) From Baseline OCT Image

| Predicted BCVA at Month 12 From Baseline OCT IMAGE | Study Eyes | | | Fellow Eyes | | | All Eyes | | |
|---|---|---|---|---|---|---|---|---|---|
|  | AUC | CI | No. | AUC | CI | No. | AUC | CI | No. |
| <69 letters at month 12 | 0.80 | 0.72, 0.87 | 126 | 0.92 | 0.88, 0.97 | 125 | 0.87 | 0.83, 0.91 | 251 |
| <59 letters at month 12 | 0.84 | 0.76, 0.92 | 126 | 0.93 | 0.88, 0.99 | 125 | 0.89 | 0.85, 0.94 | 251 |
| ≤38 letters at month 12 | 0.77 | 0.66, 0.88 | 126 | 0.96 | 0.92, 1.00 | 125 | 0.89 | 0.84, 0.95 | 251 |

AUC, area under the receiver operating characteristic curve;

BCVA best-corrected visual acuity;

OCT IMAGE, optical coherence tomography;

CI, 95% confidence interval.

Classification Model Predicting BCVA of ≤38 Letters (Snellen Equivalent, 20/200).

The deep learning model to predict month 12 BCVA of ≤38 letters from baseline OCT IMAGE had an AUC of 0.77, 0.96, and 0.89 for study eyes, fellow eyes, and all eyes, respectively (Table 8). In study eyes, the deep learning model to predict month 12 BCVA of ≤38 letters from baseline OCT IMAGE had an AUPRC=0.97 with a class balance of 114 positive eyes and 12 negative eyes. In fellow eyes, the deep learning model to predict month 12 BCVA of ≤38 letters from baseline OCT IMAGE had an AUPRC=0.99 with a class balance of 109 positive eyes and 16 negative eyes. In all eyes, the deep learning model to predict month 12 BCVA of ≤38 letters from baseline OCT IMAGE had an AUPRC=0.98 with a class balance of 223 positive eyes and 28 negative eyes.

VI.A.3. Discussion

As shown by the above results, deep learning models can predict BCVA from OCT images in subjects with neovascular AMD. The predictive accuracy of the derived model was greatest in the fellow eyes, reaching a correlation between mean predicted and mean observed BCVA ~0.92 ($R^2$=0.84, RMSE=9.01; Table 3). A moderate to strong correlation was also seen for BCVA outcomes in the study eyes, with correlations of ~0.49 ($R^2$=0.24, RMSE=11.55; Table 3) at baseline (before treatment) and ~0.79 ($R^2$=0.62, RMSE=10.54; Table 3) at month 24 (after treatment).

To benchmark the presented model results (app. RMSE 10 letter error), predictions were generated based on the screening BCVA to the baseline BCVA in the HARBOR study using simple linear regression. The average number of days between screening and baseline visits was 8.3 d with a mean change of 0.6 letters; and, for this BCVA-to-BCVA prediction the RMSE (from the regression) is 6.1 letters. This average error of 6.1 letters likely represents an information limit inherent to BCVA observations in the HARBOR study. Previous work on intersession repeatability of visual acuity scores in neovascular AMD has reported an error of approximately 12 letters. Notably, the average BCVA improvement to aVEGF treatment in the HARBOR trial was reported as 7.6-9.1 letters. The quality of deep learning prediction models used in this Example, which makes predictions from OCT IMAGE-to-BCVA, should be compared relative to the above (information) limits.

The results suggest the existence of a mapping (defined by the deep learning models) between retinal structures and visual function in neovascular AMD. Consequently, OCT images could provide a means of indirectly measuring visual function in clinical studies as well as in evolving clinical practice settings, such as telemedicine or home monitoring.

Figure 8:
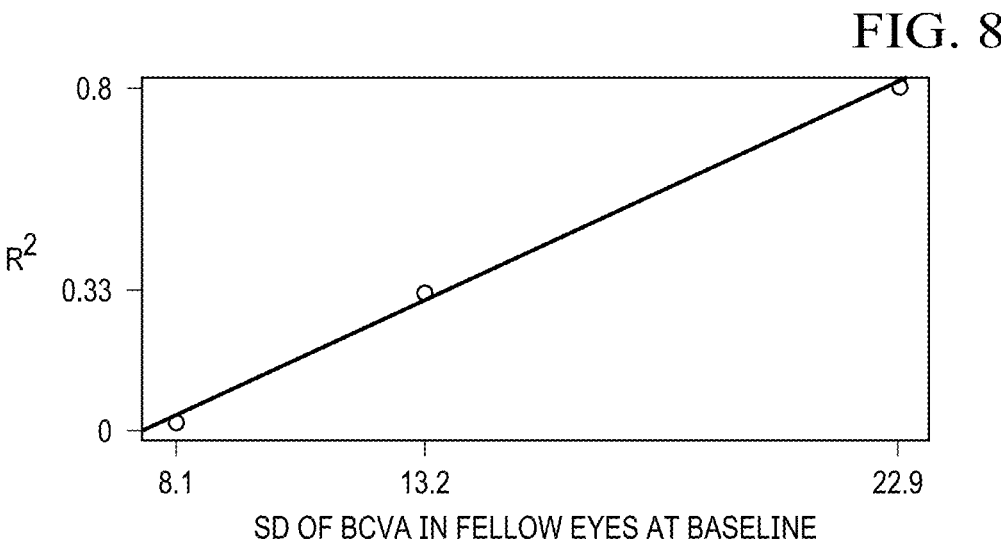
FIG. 8. Restricting standard deviation of BCVA in fellow eyes to the standard deviation of study eyes at baseline.
Figure 9:
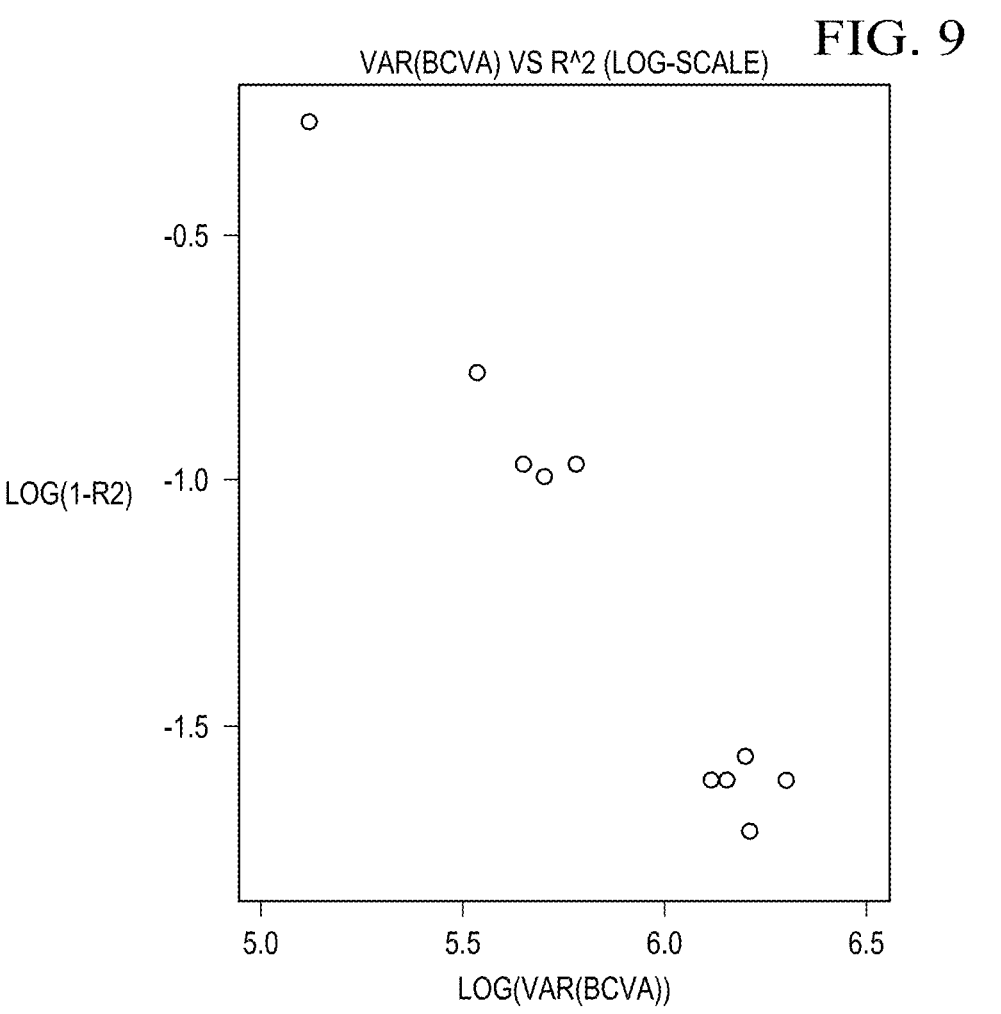
FIG. 9. $R^2$ by Variance of BCVA for Study Eyes (Black) and Fellow Eyes (Red) at Baseline, Month 6, Month 12, Month 18, and Month 24.

The difference in model performance between predicting visual function in the study eyes versus the fellow eyes was expected due to the restricted range in BCVA at baseline in the study eyes. Specifically, the eligibility criteria for HARBOR required that the study eyes have some vision loss and subfoveal CNV at baseline with BCVA between 20/40-20/320 (Snellen equivalent). These criteria were not required for the fellow eyes. Hence, the restricted range of BCVA in the study eyes at baseline (SD=13.2; Table 1) reduced the dynamic range and led to a more challenging regression task as compared with the task of predicting BCVA in the fellow eyes, which had greater variability in BCVA at baseline (baseline SD=22.9; Table 1). This observation is supported by the fact that the predictive accuracy of concurrent prediction of BCVA from OCT IMAGE increases in the study eyes over the course of the trial, along with an increase in the variability of BCVA (Tables 1-3, Table 9). This increase in range after treatment is consistent with an effective treatment producing visual improvements in many subjects. If, by simulation, the variance of BCVA was (artificially) restricted in the fellow eyes to that of the study eyes at baseline, i.e., to SD=13.2, $R^2$ decreased from 0.80 to 0.33 (FIG. 8). Similarly, if log(var(BCVA)) was plotted against log($1-R^2$) for study and fellow eyes at baseline, months 6, 12, 18, and 24, the resulting (best fitting) pattern is linear (with a slope of −1.22) and is in agreement with the theory around $R^2$ for regression and correlation models (FIG. 9). Further, as noted from the estimated residual errors (RMSE), the models seem to have similar performance at each time point (Table 3 and Table 9).

TABLE 9

Cross-validation Results. Performance of the Deep Learning Model for Regression of BCVA on OCT Image.

| | Regression of BCVA on OCT IMAGE | | | | | | | | | | | |
| | Study Eyes | | | | Fellow Eyes | | | | All Eyes | | | |
| | $R^2$ | CI | RMSE | No. | $R^2$ | CI | RMSE | No. | $R^2$ | CI | RMSE | No. |
|---|---|---|---|---|---|---|---|---|---|---|---|---|
| Baseline | 0.37 | 0.31, 0.42 | 10.14 | 793 | 0.82 | 0.80, 0.84 | 9.80 | 781 | 0.73 | 0.71, 0.76 | 10.26 | 1574 |
| Month 6 | 0.56 | 0.51, 0.60 | 10.62 | 844 | 0.79 | 0.77, 0.82 | 9.65 | 835 | 0.72 | 0.69, 0.74 | 10.16 | 1679 |
| Month 12 | 0.57 | 0.53, 0.61 | 11.05 | 809 | 0.80 | 0.78, 0.83 | 9.89 | 806 | 0.72 | 0.70, 0.75 | 10.49 | 1615 |
| Month 18 | 0.62 | 0.57, 0.66 | 10.75 | 764 | 0.80 | 0.77, 0.82 | 9.79 | 760 | 0.73 | 0.71, 0.75 | 10.28 | 1524 |
| Month 24 | 0.59 | 0.55, 0.64 | 11.45 | 769 | 0.80 | 0.77, 0.83 | 9.89 | 762 | 0.72 | 0.70, 0.75 | 10.70 | 1531 |
| All time points | 0.56 | 0.55, 0.57 | 10.81 | 21623 | 0.80 | 0.79, 0.80 | 9.94 | 21426 | 0.72 | 0.72, 0.72 | 10.41 | 43049 |
| Mean of all visits | 0.66 | 0.62, 0.69 | 8.80 | 924 | 0.85 | 0.83, 0.87 | 8.68 | 919 | 0.80 | 0.78, 0.81 | 8.74 | 1843 |

BCVA, best-corrected visual acuity;

OCT IMAGE, optical coherence tomography;

CI, 95% confidence interval;

RMSE root mean square error.

Determining the precise relationship between specific and measurable anatomical changes and vision is challenging. The conventional approach to investigating this relationship is to pick one or more anatomic features and then to perform analyses to determine if any association with vision can be quantified. As such, this approach is limited by the ability of the investigator to predetermine a potentially large set of retinal structures and features with the greatest likelihood of a meaningful relationship with visual function. In contrast, deep learning-based algorithms (and in particular CNNs) do not require any anatomic feature to be identified before the quantitative investigation. Instead, the deep learning algorithm evaluates the OCT image as a whole and learns directly from the images to identify features that enable the most accurate prediction of the outcome of interest. Compared to previously reported cross-validation results on a subset of 614 subjects from the HARBOR trial reporting an $R^2=0.34$ when using known imaging features along with baseline BCVA to predict BCVA at month 12, the regression deep learning model studied in this Example achieves an $R^2=0.45$ on the 924 subjects in the tuning set, and $R^2=0.40$ on the 126 subjects in the internal validation test set. In principle, this could lead to the identification of previously unappreciated anatomic features, or combinations of features, critical to visual function.

Separate deep learning models were able to predict the BCVA value in the study eyes 12 months from the time of the baseline OCT IMAGE measurement, with a moderate correlation of ~0.57 ($R^2=0.33$; Table 7). It is interesting to note that when added into a regression model that already contained baseline BCVA (P<0.001), the OCT IMAGE-based prediction (from baseline) remained highly statistically significant (P<0.001). In this multivariable model, both predictors provide approximately equal information of future visual function, with a model $R^2=0.40$ (Table 7). If used as a stratification factor at baseline, this prediction model could translate into smaller/shorter trials at the same statistical power. Initially, separate models were used for study and fellow eyes, but surprisingly the results were not significantly different in terms of predictive performance from the model trained on study and fellow eyes pooled together.

Use of deep learning models to predict BCVA could have meaningful clinical utility. Measurement of BCVA is frequently cumbersome, requiring specialized resources for accurate refractive testing. Indeed, in the evaluation of retinal health outside of the clinic setting, the ability to augment visual function measurements with computer vision-based analysis of OCT images will likely prove valuable for screening and monitoring subjects. For instance, it could aid remote consultations via telemedicine, where physicians can use deep learning data on the subject's current and future visual potential to support their clinical decisions. Furthermore, in clinical research, deep learning models that help predict future BCVA response could be used to support trial enrollment or trial stratification by focusing on individuals that are likely to benefit from treatment.

VI.B. Machine Learning Model for Processing Color Fundus Images to Predict Visual-Acuity Metrics The present Example assessed whether deep learning can automatically predict BCVA from color fundus photograph (CFP) images from subjects with neovascular AMD. Specifically, a first deep learning regression model (that included a deep convolutional neural network and a linear activation function) was used to predict exact BCVA from CFP images at chart distances of 2 meters (m) and 4 m. Additionally, a second deep learning classification model (that included a deep convolutional neural network and a softmax activation function) was used.

VI.B.1. Methods and Data

VI.B.1.a. Sources of Datasets

Prospectively collected BCVA measurements and CFP images taken of 707 subjects from the phase 3 MARINA clinical study (NCT00056836) and of 413 subjects from the phase 3 ANCHOR clinical study (NCT00061594) were used. MARINA and ANCHOR adhered to the tenets of the Declaration of Helsinki and was Health Insurance Portability and Accountability Act compliant. The protocol was approved by each institutional review board before study start and all subjects provided written informed consent for future medical research and analyses based on results of the trial.

In MARINA, 720 adult subjects with subfoveal choroidal neovascularization (CNV) secondary to neovascular AMD were enrolled if they had BCVA between 20/40 and 20/320 (Snellen equivalent) in the study eye using standard ETDRS charts and protocols. In ANCHOR, 426 adult subjects with subfoveal choroidal neovascularization (CNV) secondary to neovascular AMD were enrolled if they had BCVA between 20/40 and 20/320 (Snellen equivalent) in the study eye.

VI.B.1.b. CFP Images

A total of 36541 images from MARINA and 33591 images from ANCHOR were analyzed. Internal capture fields of F1M, F2, and F3M from both left and right stereo views were included in the analysis, while external views of the eye (FR capture field) were excluded. (Notably, F4, F5, F6, and/or F7 fields may have alternatively been used to predict a visual-acuity metric). To remove extraneous information, images were cropped to fit the circle produced by the camera lens. Images were then resized to 299×299×3 pixels. The CFP images from MARINA were split at the subject-level into five folds to be used for model development via cross-validation. The subjects in each fold remained constant for both regression and classification tasks.

VI.B.1.c. Outcome Variables for Deep Learning Modeling

The BCVA outcomes of interest were (1) BCVA in ETDRS letters at each visit, and (2) whether a specific BCVA value was <69 letters (Snellen equivalent 20/40). Snellen equivalent of 20/40 was chosen because it is considered to reflect functionally meaningful levels of visual acuity impairment. Mean (±standard deviation [SD]) BCVA of the eyes in the ANCHOR external validation test set was 55.7±24.7 letters for subjects with BCVA measurements taken at a distance of 2 m and 55.0±25.2 letters for subjects with BCVA measurements taken at a distance of 4 m (Table 10).

TABLE 10

Characteristics of the MARINA and ANCHOR datasets used
for model development and testing, respectively.

|  | MARINA | | ANCHOR | |
|---|---|---|---|---|
|  | BCVA @ 2 m | BCVA @ 4 m | BCVA @ 2 m | BCVA @ 4 m |
| N patients | 707 | 667 | 413 | 363 |
| N visits | 6134 | 2380 | 5655 | 1240 |
| N images | 36530 | 14161 | 33591 | 7369 |
| Mean BCVA ± SD | 55.0 ± 23.3 | 53.2 ± 24.8 | 55.7 ± 24.7 | 55.0 ± 25.2 |

VI.B.1.d. Deep Learning Algorithms

Deep learning models were evaluated for their ability to predict (1) exact BCVA value in ETDRS letters from CFP images obtained on the same visit; and (2) BCVA <69 letters (Snellen equivalent, 20/40) from CFP images obtained on the same visit.

Figure 10:
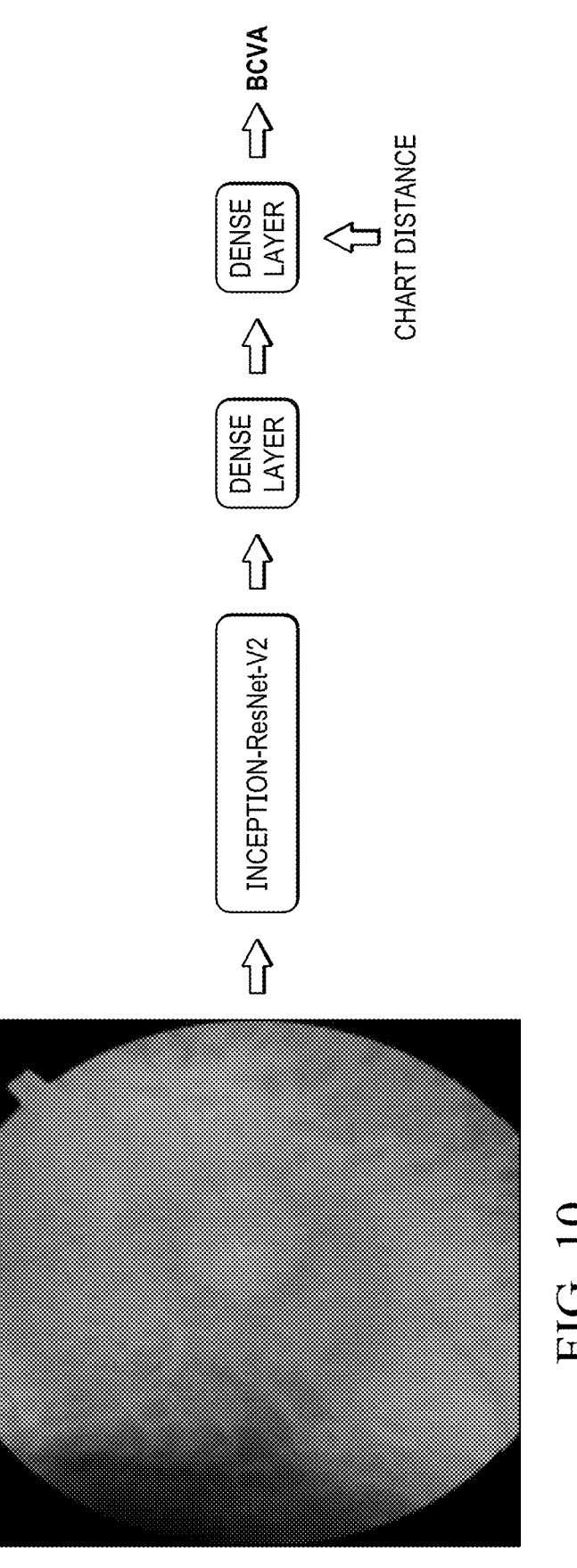
FIG. 10. Deep learning pipeline. Predicting best-corrected visual acuity (BCVA) by using color fundus photography images input to Inception ResNet-v2 convolutional neural network.

Deep learning modeling was performed using TensorFlow (1.14.0) with Keras (2.2.5) on an Nvidia V100 GPU, and the Inception-ResNet-v2 CNN architecture, which was trained to predict BCVA at the same visit as the CFP For the regression model, layers of global average pooling, dropout (0.5), dense (256), and dense (1) were added to the base CNN model. To account for the distance at which BCVA was measured, the corresponding chart distance of either 2 m or 4 m was concatenated to the final dense layer (FIG. 10). The loss function was mean squared error. For each of the five cross-validation folds, the model was initialized with weights pre-trained on the ImageNet dataset and trained for 2 epochs with the base model layers untrainable using Adam optimizer, and then trained for an additional 200 epochs with the base model layers trainable using RAdam optimizer.

For the classification model, the architecture remained the same as the regression model, except the final layer was dense (2) used a softmax activation function with a sparse categorical cross-entropy loss function. Models were initialized with the weights from the regression model for each fold. Models were trained for 3 epochs with the base model layers untrainable using Adam optimizer.

VI.B.1.e. Evaluation of the Deep Learning Models

Model weights from the epoch with the lowest validation loss were selected from each cross-validation fold. The metrics to evaluate the model fits are computed by the average of the predictions generated for an eye at each visit from each of the five cross-validation folds on the ANCHOR out-of-sample external validation test set (Table 11). Additionally, results from the MARINA five-fold cross-validation tuning set are reported (Table 11). The $R^2$ value was used to benchmark the deep learning regression models, whereas the area under the receiver operating characteristic curve (AUC) was used to assess the performance of the deep learning models for classification.

VI.B.2. Results

Regression Model Results.

Figure 11A:
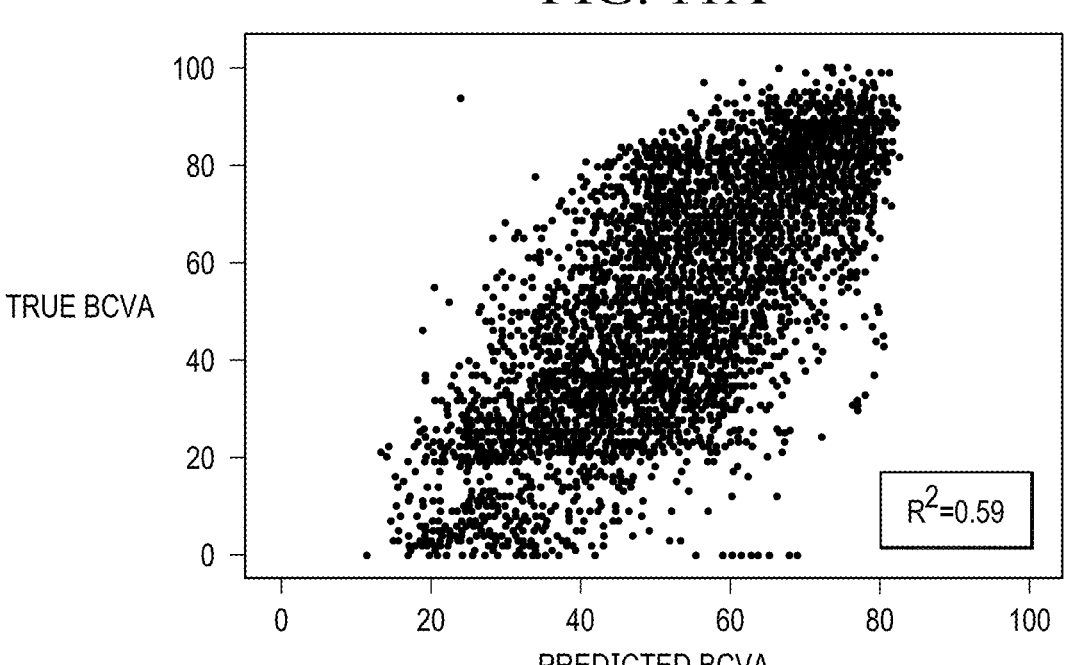
FIGS. 11A and 11B. Performance of deep learning regression model that analyzes color fundus photography images to predict BCVA in the ANCHOR external validation test set. (A) Actual versus predicted BCVA at chart distance of 2 meters. (B) Actual versus predicted BCVA at chart distance of 4 meters.
Figure 11B:
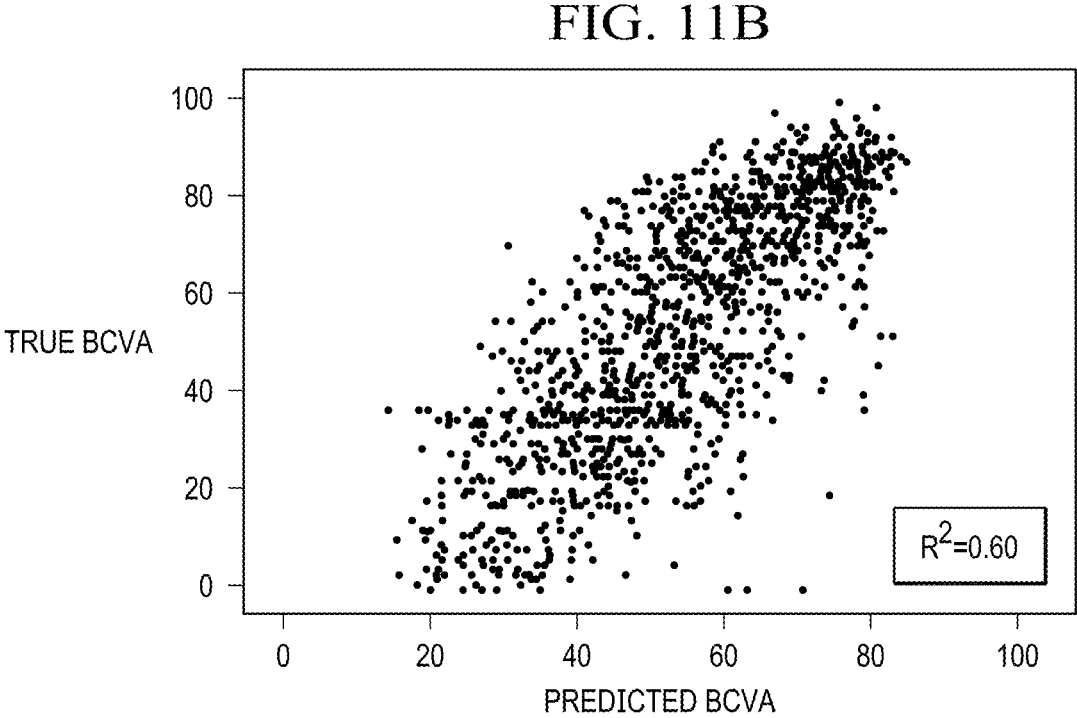

The regression model to predict BCVA at a chart distance of 2 m had an $R^2$=0.56 (95% CI: 0.54, 0.57) in the MARINA development set and an R2=0.59 (95% CI: 0.57, 0.60) in the ANCHOR external validation test set (Table 11, FIG. 11A). The regression model to predict BCVA at a chart distance of 4 m had an $R^2$=0.57 (95% CI: 0.55, 0.60) in the MARINA development set and an $R^2$=0.60 (95% CI: 0.57, 0.63) in the ANCHOR external validation test set (Table 11, FIG. 11B). FIGS. 11A and 11B show performance of the deep learning regression model, which analyzes color fundus photography images to predict BCVA in the ANCHOR external validation test set. FIG. 11A shows actual versus predicted BCVA at a chart distance of 2 meters. $R^2$=0.59. FIG. 11B shows actual versus predicted BCVA at a chart distance of 4 meters. $R^2$=0.60.

Classification Model Results.

Figure 12A:
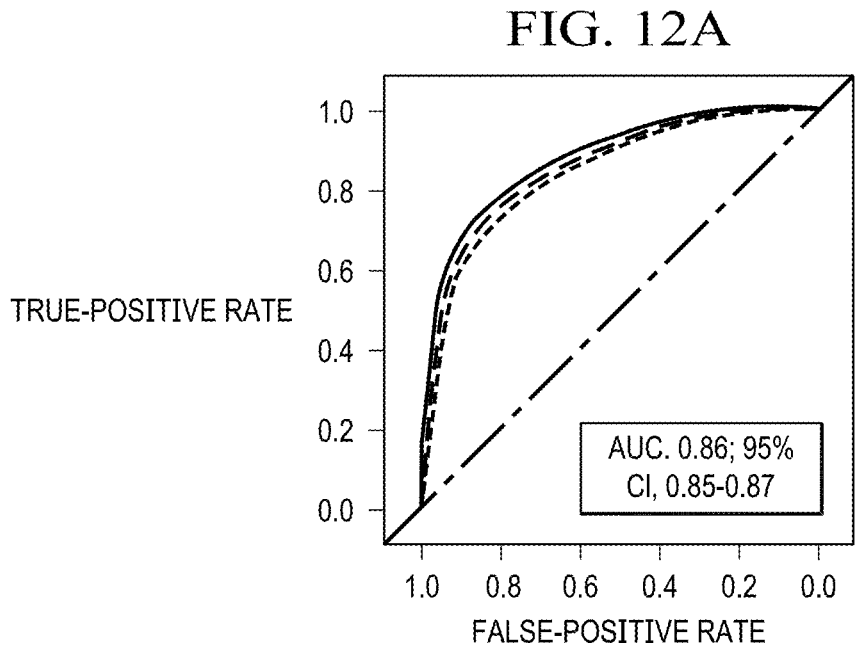
FIGS. 12A and 12B. Performance of deep learning classification model that analyzes color fundus photography images to predict BCVA <69 letters (Snellen equivalent of <20/40) in the ANCHOR external validation test set. (A) Receiver operating characteristic curve at chart distance of 2 meters. (B) Receiver operating characteristic curve at chart distance of 4 meters.
Figure 12B:
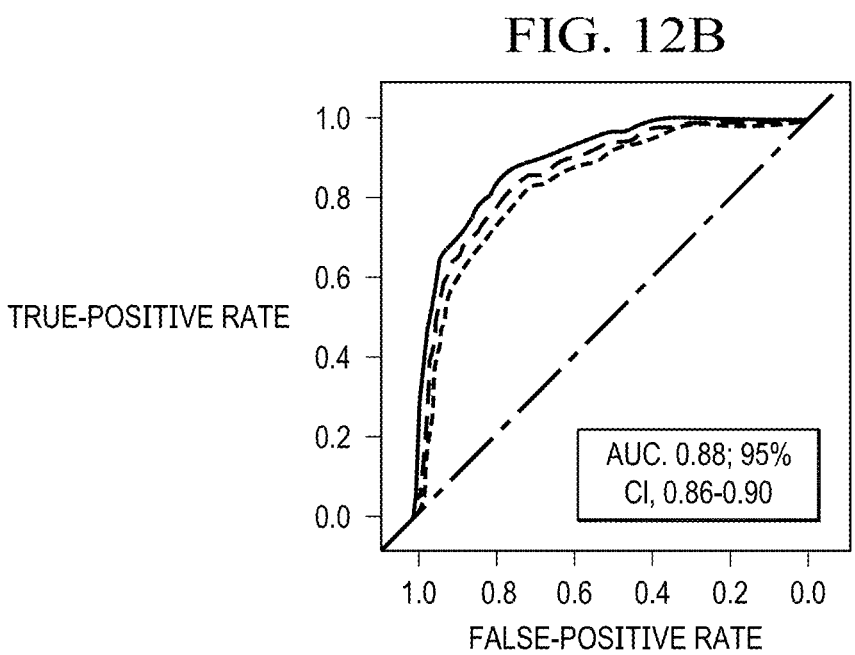

The classification model to predict BCVA <69 letters (Snellen equivalent 20/40) at a chart distance of 2 m had an AUC=0.86 (95% CI: 0.85, 0.87) in the MARINA development set and an AUC=0.86 (95% CI: 0.85, 0.87) in the ANCHOR external validation test set (Table 11, FIG. 12A). The classification model to predict BCVA <69 letters (Snellen equivalent 20/40) at a chart distance of 4 m had an AUC=0.87 (95% CI: 0.85, 0.88) in the MARINA development set and an AUC=0.88 (95% CI: 0.86, 0.90) in the ANCHOR external validation test set (Table 11, FIG. 12B). FIGS. 12A and 12B show performance of the deep learning classification model that analyzes color fundus photography images to predict BCVA <69 letters (Snellen equivalent of <20/40) in the ANCHOR external validation test set. FIG. 12A shows an area under the receiver operating characteristic curve (AUC) at a chart distance of 2 meters. AUC=0.86. FIG. 12b shows an AUC at a chart distance of 4 meters. AUC=0.88.

TABLE 11

Model performance on tuning (MARINA) and testing (ANCHOR) datasets.

|  | BCVA @ 2 m | BCVA @ 4 m |
|---|---|---|
| MARINA BCVA $R^2$ | 0.56 (95% CI: 0.54, 0.57) | 0.57 (95% CI: 0.55, 0.60) |
| ANCHOR BCVA $R^2$ | 0.59 (95% CI: 0.57, 0.60) | 0.60 (95% CI: 0.57, 0.63) |
| MARINA BCVA <69 AUC | 0.86 (95% CI: 0.85, 0.87) | 0.87 (95% CI: 0.85, 0.88) |
| ANCHOR BCVA <69 AUC | 0.86 (95% CI: 0.85, 0.87) | 0.88 (95% CI: 0.86, 0.90) |

VI.B.3. Discussion

The results demonstrate that neural networks can learn a quantitative relationship between retinal structure and visual function in subjects with neovascular age-related macular degeneration.

VII. Computing Systems

Figure 13:
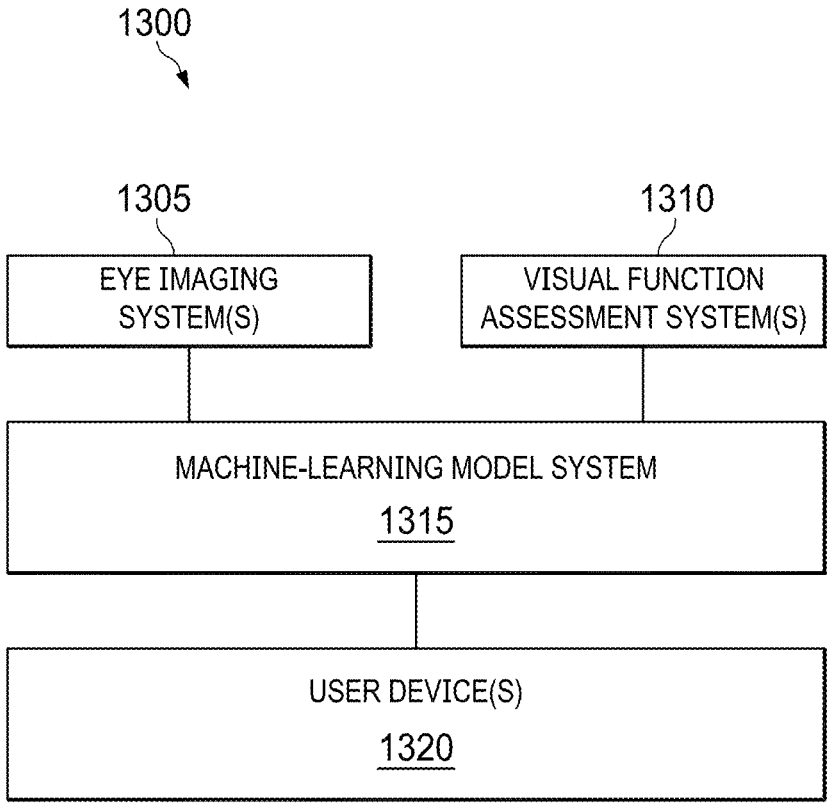
FIG. 13. Network of computing systems that can be configured to perform one or more actions and/or part or all of one more methods disclosed herein.

FIG. 13 shows a network 1300 of computing systems that can be configured to perform one or more actions and/or part or all of one more methods disclosed herein. Network 1300 can include one or more eye imaging systems 1305 configured to collect one or more images of an eye of a subject. Eye imaging system(s) can include one or more techniques disclosed herein (e.g., optical coherence tomography, disclosed in Section II.A.1, or color fundus photography, disclosed in Section II.A. 2). Eye imaging system(s) can include optical components configured to (for example) collect an OCT image or color fundus photograph. For example, eye-imaging system(s) can include an interferometer (e.g., Michelson-type interferometer), light source (e.g., low coherence, broad bandwidth) and a beamsplitter. As another example, eye-imaging system(s) can include a fundus camera. Eye imaging system(s) can include a computing system (e.g., having one or more processors, one or more memories and/or one or more transmitters) to store and/or transmit the image(s) (or a processed version thereof).

Network 1300 can include one or more visual function assessment systems 1310 that can include one or more computing systems (e.g., having one or more processors, one or more memories or one or more transmitters) configured to collect and transmit an visual-acuity metric generated based on a subject's responses to viewing a visual stimulus, such as an eye chart or eye card. The visual-acuity metric can include a metric disclosed in Section II.C.1. The visual-acuity metric can be determined based on a technique disclosed herein. In some instances, visual function assessment system(s) present the visual stimulus on a screen of the system(s). In some instances, the visual stimulus is separately presented (e.g., via a physical chart or card).

A machine-learning model system 1315 may include one or more computing systems (e.g., having one or more processors, one or more memories, one or more transmitters and/or one or more receivers). Machine-learning model system 1315 may be, in part or in its entirety, a cloud-computing system. Machine-learning model system 1315 may include one or more servers. In some instances, machine-learning model system 1315 is or is included within a subject device and/or medical device of a subject (e.g., a wearable device, smart phone, etc.).

Machine-learning model system 1315 may be configured to train and/or use a machine-learning model, which may include one or more preprocessing functions (e.g., disclosed in Section II.B.) and one or more neural networks (e.g., having an architecture and/or characteristic disclosed in Section III.A.).

Machine-learning model system 1315 can train the machine-learning model using (for example) a technique disclosed in Section III.B. Machine-learning model system 1315 may receive, for each of a set of training subjects, training data (e.g., disclosed in Section II.C). The training data may include, for each training subject, one or more images of one or both eyes (from an eye imaging system 1305) and a visual-acuity score or metric corresponding to the one or both eyes (from a visual function assessment system 1310). In some instances, for each of one or both eyes, multiple visual-acuity metrics are received corresponding to different time points (e.g., relative at a time when the image of the eye was collected). For example, one metric may correspond to a visual functional test (e.g., reading of an eye chart) administered on a same day that an image of the eye was collected, and another metric correspond to a visual function test administered approximately 6 months or approximately 1 year after the image of the eye was collected. Machine-learning model system 1315 can use the images and visual-acuity metrics to train a machine-learning model (e.g., that uses a deep convolutional network) to predict visual-acuity metrics (or another type of visual-acuity metric, such as a binary indicator) based on images of the eye. In some instances, a model includes one or more pre-processing functions to pre-process the image (s). Training the model can include learning a set of parameters.

Machine-learning model system 1315 can then receive another image corresponding to another subject (e.g., from another eye imaging system 1305) and can use the trained model to predict a current and/or future visual-acuity metric for a subject associated with the other image.

Machine-learning model system 1315 can transmit the predicted visual-acuity metric(s) to one or more user devices 1320 (e.g., along with an identifier of the subject). The one or more user devices 1320 may correspond to (for example) a care provider of the subject or the subject him/herself. A user of the one or more user devices 1320 may use the result in a manner disclosed in (for example) Section IV.

In some instances, two or more of an eye imaging system 1305, visual function assessment system 1310 or a user device 1320 are owned by a same entity, are co-located and/or are included within a same computing system (e.g., at a care provider's office). In some instances, a device of a subject (e.g., a smart phone) includes at least part of each of two or more depicted components. For example, an accessory to a smart phone may be used to collect an image of the subject's eye, a trained machine-learning model can be locally run on the smart phone and a predicted visual-acuity can be availed to the smart phone.

VIII. Exemplary Embodiments

A first exemplary example includes a method for predicting visual acuity based on image processing. The method includes accessing an image of at least part of an eye of a subject; inputting the image into a machine-learning model to determine a predicted visual-acuity metric corresponding to a predicted visual acuity, where the machine-learning model includes: a set of parameters determined using: a set of training images, each of the set of training images depicting at least part of an eye of a training subject of a set of training subjects; and a set of labels identifying an observed visual acuity for each of the set of training subjects; and further using a function relating the image and the parameters to a visual-acuity metric (e.g. where the function is learned to relate training images to observed visual-acuity metrics and where the function can be used to relate non-training images to predicted visual-acuity metrics); and returning the predicted visual-acuity metric.

A second exemplary example includes the first exemplary example, where the image is an optical coherence tomography (OCT) image.

A third exemplary example includes the first exemplary example, where the image is a color fundus photograph image.

A fourth exemplary example includes any of the first through third exemplary examples, where the predicted visual-acuity metric corresponds to a predicted visual acuity on a baseline date when the image was captured by an imaging device.

A fifth exemplary example includes any of the first through third exemplary examples, where the predicted visual-acuity metric includes one or more numbers, the one or more numbers representing a predicted visual acuity on a date at least 6 months from a baseline date when the image was captured.

A sixth exemplary example includes any of the first through third exemplary examples, where the predicted visual-acuity metric is a binary value representing a prediction as to whether a visual acuity of the subject, on a baseline date when the image was captured by an imaging device, was worse than a threshold visual-acuity value.

A seventh exemplary example includes any of the first through third exemplary examples, where the predicted visual-acuity metric is a binary value representing a prediction as to whether a visual acuity of the subject, on at least 6 months from a baseline date when the image was captured by an imaging device, was worse than a threshold visual-acuity value.

A eighth exemplary example includes the sixth or seventh exemplary example, where the threshold is equivalent to a Snellen fraction of 20/160, 20/80 or 20/40.

A ninth exemplary example includes any of the first through eighth exemplary examples, further including, responsive to the predicted visual-acuity metric:

providing a recommendation that the subject receive a pharmacological treatment.

A tenth exemplary example includes any of the first through ninth exemplary examples, where the image is a three dimensional image, and where the method further includes:

slicing the image into a plurality two-dimensional slices, each of the slices captured at a different scan-centered angle and offset a different number pixels from each other slice; and where inputting the image into the model includes inputting the slices into the model.

An eleventh exemplary example includes any of the first through tenth exemplary examples, where the model is a deep learning model.

A twelfth exemplary example includes any of the first through eleventh exemplary examples, where the model is or includes a convolutional neural network.

A thirteenth exemplary example includes any of the first through twelfth exemplary examples where the model uses a set of convolution kernels.

A fourteenth exemplary example includes any of the first through thirteenth exemplary examples where the model includes a ResNet model.

A fifteenth exemplary example includes any of the first through fourteenth exemplary examples where the model is an Inception model.

A sixteenth exemplary example includes any of the first through fifteenth exemplary examples where the predicted visual-acuity metric corresponds to a predicted visual acuity for the eye of the subject.

A seventeenth exemplary example includes any of the first through sixteenth exemplary examples where the predicted visual-acuity metric corresponds to a predicted corrected visual acuity that predicts a visual acuity of the eye subject while wearing glasses or contacts.

An eighteenth exemplary example includes any of the first through seventeenth exemplary examples where the pre-dicted visual-acuity metric corresponds to a predicted best corrected visual acuity for the eye of subject.

A nineteenth exemplary example includes any of the first through seventeenth exemplary examples where the subject was previously diagnosed with age-related macular degeneration at a time at which the image was collected.

A twentieth exemplary example includes any of the first through seventeenth exemplary examples where the subject was previously diagnosed with neovascular age-related macular degeneration at a time at which the image was collected.

A twenty-first exemplary example includes any of the first through seventeenth exemplary examples where the subject was previously diagnosed with atrophic age-related macular degeneration at a time at which the image was collected.

A twenty-second exemplary example includes any of the first through seventeenth exemplary examples where each of the training subjects was previously diagnosed with age-related macular degeneration prior to a training image of the set of images having been collected.

A twenty-third exemplary example includes any of the first through seventeenth exemplary examples where each of the training subjects was previously diagnosed with neovascular age-related macular degeneration prior to a training image of the set of images having been collected.

A twenty-fourth exemplary example includes any of the first through seventeenth exemplary examples where each of the training subjects was previously diagnosed with atrophic age-related macular degeneration prior to a training image of the set of images having been collected.

A twenty-fifth exemplary example includes any of the first through twenty-fourth exemplary examples further including:

training the model using the set of training images and the set of labels.

A twenty-sixth exemplary example includes any of the first through twenty-fifth exemplary examples where the machine-learning model includes one or more preprocessing functions and one or more neural networks.

A twenty-seventh exemplary example includes any of the first through twenty-fifth exemplary examples where the image of the at least part of the eye includes a preprocessed version of an eye generated by applying one or more preprocessing functions to a raw image of the at least part of the eye of the subject.

A twenty-eighth exemplary example includes any of the twenty-sixth or twenty-seventh exemplary examples where the one or more preprocessing functions includes a function to flatten an image.

A twenty-ninth exemplary example includes any of the twenty-sixth or twenty-seventh exemplary examples where the one or more preprocessing functions includes a function to generate one or more B-scans images or one or more C-scan images.

A thirtieth exemplary example includes any of the twenty-sixth or twenty-ninth exemplary examples where the one or more preprocessing functions includes a cropping function.

A thirty-first exemplary example includes any of the twenty-sixth or twenty-ninth where the predicted visual-acuity metric corresponds to a predicted visual acuity for the eye of the subject at a first distance, and where the method further includes:

using the machine-learning model to determine another predicted visual-acuity metric corresponding to a predicted visual acuity for a same or different eye of the subject; and returning the other predicted visual-acuity metric.

A thirty-second exemplary example includes a method of stratifying a clinical study, the method including performing, for each subject of a set of subjects, the method for predicting visual acuity based on image processing of any of the first through thirty-first exemplary examples; determining, for each of the set of subjects, whether the subject is eligible to participate in a clinical study, where the determination is based on whether each of a set of eligibility criteria is satisfied in relation to the subject, and where evaluation of a particular eligibility criterion of the set of eligibility criteria is performed using the predicted visual acuity for the subject; and performing the clinical study with a subset of the set of subjects, where each subject in the subset was determined to be eligible to participate in the clinical study.

A thirty-third exemplary example includes the thirty-second exemplary example, further including conducting the clinical study in accordance with the subject assignments to the first and second subject groups.

A thirty-fourth exemplary example includes a method including selecting, based on the predicted visual-acuity metric determined in accordance with the method of any of the first through thirty-first exemplary examples, a treatment from among a set of potential treatments for the subject; and outputting an identification of the treatment.

A thirty-fifth exemplary example includes selecting, based on the predicted visual-acuity metric determined in accordance with any of the first through thirty-first exemplary examples, a treatment from among a set of potential treatments for the subject; and treating the subject using the treatment.

A thirty-sixth exemplary example includes the thirty-fourth or thirty-fifth exemplary example, where each of at least some of the training subjects had received the treatment prior to having participated in a visual-acuity sight test from which the label corresponding to the training subject was determined.

A thirty-seventh exemplary example includes the thirty-fourth or thirty-fifth exemplary example, where each of the training subjects had received the treatment prior to having participated in a visual-acuity sight test from which the label corresponding to the training subject was determined.

A thirty-eighth exemplary example includes the thirty-fourth or thirty-fifth exemplary example, where each of at least some of the training subjects had received another treatment different than the treatment prior to having participated in a visual-acuity sight test from which the label corresponding to the training subject was determined, where the subject was previously receiving the other treatment.

A thirty-ninth exemplary example includes the thirty-fourth or thirty-fifth exemplary example, where each of the training subjects had received another treatment different than the treatment prior to having participated in a visual-acuity sight test from which the label corresponding to the training subject was determined, where the subject was previously receiving the other treatment.

A fortieth exemplary example includes one or more data processors; and a non-transitory computer readable storage medium containing instructions which, when executed on the one or more data processors, cause the one or more data processors to perform part or all of one or more methods disclosed herein.

A forty-first exemplary example includes a computer-program product tangibly embodied in a non-transitory machine-readable storage medium, including instructions configured to cause one or more data processors to perform part or all of one or more methods disclosed herein.

IX. Additional Considerations

Some disclosures herein refer to a subject (e.g., identifying a subject's visual acuity, predicting a subject's visual acuity, treating a subject, etc.). It will be appreciated that, in some embodiments, some or all of these disclosures pertain to a specific eye of the subject.

Some embodiments of the present disclosure include a system including one or more data processors. In some embodiments, the system includes a non-transitory computer readable storage medium containing instructions which, when executed on the one or more data processors, cause the one or more data processors to perform part or all of one or more methods and/or part or all of one or more processes disclosed herein. Some embodiments of the present disclosure include a computer-program product tangibly embodied in a non-transitory machine-readable storage medium, including instructions configured to cause one or more data processors to perform part or all of one or more methods and/or part or all of one or more processes disclosed herein.

The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention as claimed has been specifically disclosed by embodiments and optional features, modification and variation of the concepts herein disclosed may be resorted to by those skilled in the art, and that such modifications and variations are considered to be within the scope of this invention as defined by the appended claims.

The description provides preferred exemplary embodiments only, and is not intended to limit the scope, applicability or configuration of the disclosure. Rather, the description of the preferred exemplary embodiments will provide those skilled in the art with an enabling description for implementing various embodiments. It is understood that various changes may be made in the function and arrangement of elements without departing from the spirit and scope as set forth in the appended claims.

Specific details are given in the following description to provide a thorough understanding of the embodiments. However, it will be understood that the embodiments may be practiced without these specific details. For example, circuits, systems, networks, processes, and other components may be shown as components in block diagram form in order not to obscure the embodiments in unnecessary detail. In other instances, well-known circuits, processes, algorithms, structures, and techniques may be shown without unnecessary detail in order to avoid obscuring the embodiments.

What is claimed is:

1. A method for predicting visual acuity based on image processing, the method comprising:
   accessing an image of at least part of an eye of a subject, wherein the image was captured by an imaging device on a first date;
   inputting the image into a machine-learning model to determine:
   a first predicted visual-acuity metric that predicts a visual acuity of the subject as would be determined based on performing a visual-acuity assessment of the subject on the first date on which the image was captured; and a second predicted visual-acuity metric that predicts the visual acuity of the subject as would be determined based on performing the visual-acuity assessment of the subject on a second date that is at a specified interval after the first date, wherein the machine-learning model comprises:

a set of parameters determined using:

a set of training images corresponding to a set of training subjects, wherein each image of the set of training images depicts at least part of an eye of a corresponding training subject of the set of training subjects;

wherein the set of training images comprises a first set of training images and a second set of training images;

and a set of labels identifying an observed visual acuity metric for each subject of the set of training subjects;

wherein the observed visual acuity metric comprises a numeric visual acuity value and/or an identification of a numerical visual-acuity range; and wherein the set of labels comprise a first set of labels and a second set of labels;

wherein the first set of labels are associated with the first set of training images and identify the observed visual acuity metric for each subject of the set of training subjects at the time that the image was collected; and wherein the second set of labels are associated with the second set of training images and identify the observed visual acuity metric for each subject of the set of training subjects at a time after the image was collected;

and a function relating the image and the set of parameters to the first predicted visual-acuity metric and the second predicted visual-acuity metric;

and returning the first predicted visual-acuity metric and the second predicted visual acuity metric.

2. The method of claim 1, wherein the image is an optical coherence tomography (OCT) image.

3. The method of claim 1, wherein the image is a color fundus photograph image.

4. The method of claim 1, wherein the second date is 12 months after the first date.

5. The method of claim 1, wherein the second predicted visual-acuity metric includes one or more numbers, the one or more numbers representing the second predicted visual acuity on the second date, wherein the second date is at least 6 months after the first date when the image was captured.

6. The method of claim 1, wherein the first predicted visual-acuity metric is a binary value that predicts whether the first predicted visual acuity of the subject on the first date was worse than a threshold visual-acuity value.

7. The method of claim 1, wherein the second predicted visual-acuity metric is a binary value that predicts whether the second predicted visual acuity of the subject was worse than a threshold visual-acuity value, wherein the second date is at least 6 months after the first date.

8. The method of claim 7 wherein the threshold visual-acuity value is a Snellen fraction of 20/160, 20/80 or 20/40.

9. The method of claim 1, further comprising, responsive to the first predicted visual-acuity metric and the second predicted visual-acuity metric: providing a recommendation that the subject receive a pharmacological treatment.

10. The method of claim 1, wherein the image is a three-dimensional image, and wherein the method further comprises:

slicing the image into a plurality of two-dimensional slices, each slice of the plurality of two-dimensional slices captured at a different scan-centered angle and offset a different number of pixels from each other slice; and wherein inputting the image into the machine-learning model comprises inputting the plurality of two-dimensional slices into the machine-learning model.

11. The method of claim 1, wherein the machine-learning model is a deep learning model.

12. The method of claim 1, wherein the machine-learning model is or includes a convolutional neural network.

13. The method of claim 1, wherein the machine-learning model uses a set of convolution kernels.

14. The method of claim 1, wherein the machine-learning model includes at least one of a ResNet model or an Inception model.

15. The method of claim 1, wherein the visual-acuity assessment evaluates a response of the subject to one or more visual stimuli.

16. A method of stratifying a clinical study, the method comprising:

performing, for each subject of a set of subjects, the method for predicting visual acuity based on image processing of claim 1;

determining, for each of the set of subjects, whether the subject is eligible to participate in a clinical study, wherein the determination is based on whether each of a set of eligibility criteria is satisfied in relation to the subject, and wherein evaluation of a particular eligibility criterion of the set of eligibility criteria is performed using at least one of the first predicted visual-acuity metric and the second predicted visual-acuity metric for the subject; and wherein the clinical study is determined to be performed with a subset of the set of subjects, wherein each subject in the subset was determined to be eligible to participate in the clinical study.

17. The method of claim 16, wherein the clinical study is determined to be conducted in accordance with subject assignments to first and second subject groups.

18. The method of claim 1, wherein the observed visual acuity metric comprises the numeric visual acuity value.

19. The method of claim 1, further comprising returning a predicted rate of decline of visual acuity of the subject.

20. A system comprising:

one or more data processors; and a non-transitory computer readable storage medium containing instructions which, when executed on the one or more data processors, cause the one or more data processors to:

access an image of at least part of an eye of a subject, wherein the image was captured by an imaging device on a first date;

input the image into a machine-learning model to determine:

a first predicted visual-acuity metric that predicts a visual acuity of the subject as would be determined based on performing a visual-acuity assessment of the subject on the first date on which the image was captured; and a second predicted visual-acuity metric that predicts the visual acuity of the subject as would be determined based on performing the visual-acuity assessment of the subject on a second date that is at a specified interval after the first date, wherein the machine-learning model comprises:

a set of parameters determined using:

a set of training images corresponding to a set of training subjects, wherein each image of the set of training images depicts at least part of an eye of a corresponding training subject of the set of training subjects;

wherein the set of training images comprises a first set of training images and a second set of training images;

and a set of labels identifying an observed visual acuity metric for each subject of the set of training subjects;

wherein the observed visual acuity metric comprises a numeric visual acuity value and/or an identification of a numerical visual-acuity range; and wherein the set of labels comprise a first set of labels and a second set of labels;

wherein the first set of labels are associated with the first set of training images and identify the observed visual acuity metric for each subject of the set of training subjects at the time that the image was collected; and wherein the second set of labels are associated with the second set of training images and identify the observed visual acuity metric for each subject of the set of training subjects at a time after the image was collected;

and a function relating the image and the set of parameters to the first predicted visual-acuity metric and the second predicted visual-acuity metric; and return the first predicted visual-acuity metric and the second predicted visual-acuity metric.

21. The system of claim 20, wherein the observed visual acuity metric comprises the numeric visual acuity value.

* * * * *